United States Patent
Morun et al.

(10) Patent No.: US 10,362,958 B2
(45) Date of Patent: *Jul. 30, 2019

(54) SYSTEMS, ARTICLES, AND METHODS FOR ELECTROMYOGRAPHY SENSORS

(71) Applicant: CTRL-labs Corporation, New York, NY (US)

(72) Inventors: Cezar Morun, Kitchener (CA); Stephen Lake, Kitchener (CA)

(73) Assignee: CTRL-labs Corporation, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/057,573

(22) Filed: Aug. 7, 2018

(65) Prior Publication Data

US 2018/0344195 A1 Dec. 6, 2018

Related U.S. Application Data

(63) Continuation of application No. 14/553,657, filed on Nov. 25, 2014, now Pat. No. 10,188,309.
(Continued)

(51) Int. Cl.
*A61B 5/0492* (2006.01)
*H05K 1/16* (2006.01)

(52) U.S. Cl.
CPC .......... *A61B 5/0492* (2013.01); *H05K 1/162* (2013.01); *H05K 1/167* (2013.01);
(Continued)

(58) Field of Classification Search
CPC ............... A61B 5/0492; H05K 1/162
(Continued)

(56) References Cited

U.S. PATENT DOCUMENTS 1,411,995 A 4/1922 Dull
3,620,208 A 11/1971 Higley et al.
(Continued)

FOREIGN PATENT DOCUMENTS

CN 102246125 A 11/2011
DE 44 12 278 A1 10/1995
(Continued)

OTHER PUBLICATIONS

Brownlee, "Finite State Machines (FSM): Finite state machines as a control technique in Artificial Intelligence (AI)," Jun. 2002, 12 pages.
(Continued)

*Primary Examiner* — Nadia A Mahmood
(74) *Attorney, Agent, or Firm* — Wolf, Greenfield & Sacks, P.C.

(57) ABSTRACT

Systems, articles, and methods for surface electromyography ("EMG") sensors that combine elements from traditional capacitive and resistive EMG sensors are described. For example, capacitive EMG sensors that are adapted to resistively couple to a user's skin are described. Resistive coupling between a sensor electrode and the user's skin is galvanically isolated from the sensor circuitry by a discrete component capacitor included downstream from the sensor electrode. The combination of a resistively coupled electrode and a discrete component capacitor provides the respective benefits of traditional resistive and capacitive (respectively) EMG sensor designs while mitigating respective drawbacks of each approach. A wearable EMG device that provides a component of a human-electronics interface and incorporates such capacitive EMG sensors is also described.

24 Claims, 6 Drawing Sheets

Related U.S. Application Data

(60) Provisional application No. 61/909,786, filed on Nov. 27, 2013.

(52) U.S. Cl.
CPC .............. *H05K 2201/10151* (2013.01); *H05K 2201/10166* (2013.01); *Y10T 29/4913* (2015.01)

(58) Field of Classification Search
USPC ........................................................ 600/393
See application file for complete search history.

(56) References Cited

U.S. PATENT DOCUMENTS

| | | |
|---|---|---|
| 3,880,146 A | 4/1975 | Everett et al. |
| 4,602,639 A | 7/1986 | Hoogendoorn et al. |
| 4,705,408 A | 11/1987 | Jordi |
| 4,817,064 A | 3/1989 | Milles |
| 5,003,978 A | 4/1991 | Dunseath, Jr. |
| D322,227 S | 12/1991 | Warhol |
| 5,081,852 A | 1/1992 | Cox |
| 5,251,189 A | 10/1993 | Thorp |
| D348,660 S | 7/1994 | Parsons |
| 5,445,869 A | 8/1995 | Ishikawa et al. |
| 5,482,051 A | 1/1996 | Reddy et al. |
| 5,605,059 A | 2/1997 | Woodward |
| 5,683,404 A | 11/1997 | Johnson |
| 6,032,530 A | 3/2000 | Hock |
| 6,184,847 B1 | 2/2001 | Fateh et al. |
| 6,238,338 B1 | 5/2001 | DeLuca et al. |
| 6,244,873 B1 | 6/2001 | Hill et al. |
| 6,377,277 B1 | 4/2002 | Yamamoto |
| D459,352 S | 6/2002 | Giovanniello |
| 6,487,906 B1 | 12/2002 | Hock |
| 6,510,333 B1 | 1/2003 | Licata et al. |
| 6,527,711 B1 | 3/2003 | Stivoric et al. |
| 6,619,836 B1 | 9/2003 | Silvant et al. |
| 6,720,984 B1 | 4/2004 | Jorgensen et al. |
| 6,743,982 B2 | 6/2004 | Biegelsen et al. |
| 6,807,438 B1 | 10/2004 | Brun del Re et al. |
| D502,661 S | 3/2005 | Rapport |
| D502,662 S | 3/2005 | Rapport |
| 6,865,409 B2 | 3/2005 | Getsla et al. |
| D503,646 S | 4/2005 | Rapport |
| 6,880,364 B1 | 4/2005 | Vidolin et al. |
| 6,927,343 B2 | 8/2005 | Watanabe et al. |
| 6,965,842 B2 | 11/2005 | Rekimoto |
| 6,972,734 B1 | 12/2005 | Ohshima et al. |
| 6,984,208 B2 | 1/2006 | Zheng |
| 7,022,919 B2 | 4/2006 | Brist et al. |
| 7,028,507 B2 | 4/2006 | Rapport |
| 7,086,218 B1 | 8/2006 | Pasach |
| D535,401 S | 1/2007 | Travis et al. |
| 7,173,437 B2 | 2/2007 | Hervieux et al. |
| 7,209,114 B2 | 4/2007 | Radley-Smith |
| D543,212 S | 5/2007 | Marks |
| 7,265,298 B2 | 9/2007 | Maghribi et al. |
| 7,271,774 B2 | 9/2007 | Puuri |
| 7,333,090 B2 | 2/2008 | Tanaka et al. |
| 7,450,107 B2 | 11/2008 | Radley-Smith |
| 7,491,892 B2 | 2/2009 | Wagner et al. |
| 7,517,725 B2 | 4/2009 | Reis |
| 7,558,622 B2 | 7/2009 | Tran |
| 7,596,393 B2 | 9/2009 | Jung et al. |
| 7,618,260 B2 | 11/2009 | Daniel et al. |
| 7,636,549 B2 | 12/2009 | Ma et al. |
| 7,640,007 B2 | 12/2009 | Chen et al. |
| 7,660,126 B2 | 2/2010 | Cho et al. |
| 7,809,435 B1 | 10/2010 | Ettare et al. |
| 7,844,310 B2 | 11/2010 | Anderson |
| 7,870,211 B2 | 1/2011 | Pascal et al. |
| 7,925,100 B2 | 4/2011 | Howell et al. |
| 7,948,763 B2 | 5/2011 | Chuang |
| D643,428 S | 8/2011 | Janky et al. |
| D646,192 S | 10/2011 | Woode |
| 8,054,061 B2 | 11/2011 | Prance et al. |
| D654,622 S | 2/2012 | Hsu |
| 8,170,656 B2 | 5/2012 | Tan et al. |
| 8,179,604 B1 | 5/2012 | Prada Gomez et al. |
| 8,188,937 B1 | 5/2012 | Amafuji et al. |
| D661,613 S | 6/2012 | Demeglio |
| 8,203,502 B1 | 6/2012 | Chi et al. |
| 8,207,473 B2 | 6/2012 | Axisa et al. |
| 8,212,859 B2 | 7/2012 | Tang et al. |
| 8,355,671 B2 | 1/2013 | Kramer et al. |
| 8,389,862 B2 | 3/2013 | Arora et al. |
| 8,421,634 B2 | 4/2013 | Tan et al. |
| 8,427,977 B2 | 4/2013 | Workman et al. |
| D682,727 S | 5/2013 | Bulgari |
| 8,447,704 B2 | 5/2013 | Tan et al. |
| 8,467,270 B2 | 6/2013 | Gossweiler, III et al. |
| 8,469,741 B2 | 6/2013 | Oster et al. |
| D689,862 S | 9/2013 | Liu |
| 8,591,411 B2 | 11/2013 | Banet et al. |
| D695,454 S | 12/2013 | Moore |
| 8,620,361 B2 | 12/2013 | Bailey et al. |
| 8,624,124 B2 | 1/2014 | Koo et al. |
| 8,702,629 B2 | 4/2014 | Giuffrida et al. |
| 8,704,882 B2 | 4/2014 | Turner |
| 8,777,668 B2 | 7/2014 | Ikeda et al. |
| D716,457 S | 10/2014 | Brefka et al. |
| D717,685 S | 11/2014 | Bailey et al. |
| 8,879,276 B2 | 11/2014 | Wang |
| 8,883,287 B2 | 11/2014 | Boyce et al. |
| 8,895,865 B2 | 11/2014 | Lenahan et al. |
| 8,912,094 B2 | 12/2014 | Koo et al. |
| 8,922,481 B1 | 12/2014 | Kauffmann et al. |
| 8,954,135 B2 | 2/2015 | Yuen et al. |
| 8,970,571 B1 | 3/2015 | Wong et al. |
| 8,971,023 B2 | 3/2015 | Olsson et al. |
| 9,018,532 B2 | 4/2015 | Wesselmann et al. |
| 9,086,687 B2 | 7/2015 | Park et al. |
| D736,664 S | 8/2015 | Paradise et al. |
| 9,146,730 B2 | 9/2015 | Lazar |
| D741,855 S | 10/2015 | Park et al. |
| D742,272 S | 11/2015 | Bailey et al. |
| D742,874 S | 11/2015 | Cheng et al. |
| D743,963 S | 11/2015 | Osterhout |
| 9,211,417 B2 | 12/2015 | Heldman et al. |
| D747,714 S | 1/2016 | Erbeus |
| D750,623 S | 3/2016 | Park et al. |
| D751,065 S | 3/2016 | Magi |
| 9,299,248 B2 | 3/2016 | Lake et al. |
| D756,359 S | 5/2016 | Bailey et al. |
| 9,367,139 B2 | 6/2016 | Ataee et al. |
| 9,372,535 B2 | 6/2016 | Bailey et al. |
| 9,389,694 B2 | 7/2016 | Ataee et al. |
| 9,393,418 B2 | 7/2016 | Giuffrida et al. |
| 9,408,316 B2 | 8/2016 | Bailey et al. |
| 9,418,927 B2 | 8/2016 | Axisa et al. |
| 9,439,566 B2 | 9/2016 | Arne et al. |
| 9,472,956 B2 | 10/2016 | Michaelis et al. |
| 9,477,313 B2 | 10/2016 | Mistry et al. |
| 9,483,123 B2 | 11/2016 | Aleem et al. |
| 9,529,434 B2 | 12/2016 | Choi et al. |
| 9,600,030 B2 | 3/2017 | Bailey et al. |
| 9,788,789 B2 | 10/2017 | Bailey |
| 9,807,221 B2 | 10/2017 | Bailey et al. |
| 2002/0032386 A1 | 3/2002 | Sackner et al. |
| 2002/0077534 A1 | 6/2002 | DuRousseau |
| 2003/0036691 A1 | 2/2003 | Stanaland et al. |
| 2003/0051505 A1 | 3/2003 | Robertson et al. |
| 2003/0144586 A1 | 7/2003 | Tsubata |
| 2004/0073104 A1 | 4/2004 | Brun del Re et al. |
| 2004/0194500 A1 | 10/2004 | Rapport |
| 2004/0210165 A1 | 10/2004 | Marmaropoulos et al. |
| 2005/0012715 A1 | 1/2005 | Ford |
| 2005/0070227 A1 | 3/2005 | Shen et al. |
| 2005/0119701 A1 | 6/2005 | Lauter et al. |
| 2005/0177038 A1 | 8/2005 | Kolpin et al. |
| 2006/0037359 A1 | 2/2006 | Stinespring |
| 2006/0061544 A1 | 3/2006 | Min et al. |
| 2007/0132785 A1 | 6/2007 | Ebersole, Jr. et al. |

(56) References Cited

U.S. PATENT DOCUMENTS

| | | |
|---|---|---|
| 2008/0136775 A1 | 6/2008 | Conant |
| 2009/0007597 A1 | 1/2009 | Hanevold |
| 2009/0031757 A1 | 2/2009 | Harding |
| 2009/0040016 A1 | 2/2009 | Ikeda |
| 2009/0051544 A1 | 2/2009 | Niknejad |
| 2009/0102580 A1 | 4/2009 | Uchaykin |
| 2009/0109241 A1 | 4/2009 | Tsujimoto |
| 2009/0147004 A1 | 6/2009 | Ramon et al. |
| 2009/0179824 A1 | 7/2009 | Tsujimoto et al. |
| 2009/0189867 A1 | 7/2009 | Krah et al. |
| 2009/0251407 A1 | 10/2009 | Flake et al. |
| 2009/0258669 A1 | 10/2009 | Nie et al. |
| 2009/0318785 A1 | 12/2009 | Ishikawa et al. |
| 2010/0041974 A1 | 2/2010 | Ting et al. |
| 2010/0280628 A1 | 11/2010 | Sankai |
| 2010/0293115 A1 | 11/2010 | Seyed Momen |
| 2010/0317958 A1 | 12/2010 | Beck et al. |
| 2011/0018754 A1 | 1/2011 | Tojima et al. |
| 2011/0054360 A1 | 3/2011 | Son et al. |
| 2011/0072510 A1 | 3/2011 | Cheswick |
| 2011/0134026 A1 | 6/2011 | Kang et al. |
| 2011/0166434 A1 | 7/2011 | Gargiulo |
| 2011/0172503 A1 | 7/2011 | Knepper et al. |
| 2011/0181527 A1 | 7/2011 | Capela et al. |
| 2011/0213278 A1 | 9/2011 | Horak et al. |
| 2011/0224556 A1 | 9/2011 | Moon et al. |
| 2011/0224564 A1 | 9/2011 | Moon et al. |
| 2012/0029322 A1 | 2/2012 | Wartena et al. |
| 2012/0051005 A1 | 3/2012 | Vanfleteren et al. |
| 2012/0053439 A1 | 3/2012 | Ylostalo et al. |
| 2012/0071092 A1 | 3/2012 | Pasquero et al. |
| 2012/0101357 A1 | 4/2012 | Hoskuldsson et al. |
| 2012/0157789 A1 | 6/2012 | Kangas et al. |
| 2012/0157886 A1 | 6/2012 | Tenn et al. |
| 2012/0165695 A1 | 6/2012 | Kidmose et al. |
| 2012/0182309 A1 | 7/2012 | Griffin et al. |
| 2012/0188158 A1 | 7/2012 | Tan et al. |
| 2012/0203076 A1 | 8/2012 | Fatta et al. |
| 2012/0209134 A1 | 8/2012 | Morita et al. |
| 2012/0226130 A1 | 9/2012 | De Graff et al. |
| 2012/0265090 A1 | 10/2012 | Fink et al. |
| 2012/0283896 A1 | 11/2012 | Persaud et al. |
| 2012/0293548 A1 | 11/2012 | Perez et al. |
| 2012/0302858 A1 | 11/2012 | Kidmose et al. |
| 2012/0323521 A1 | 12/2012 | De Foras et al. |
| 2013/0005303 A1 | 1/2013 | Song et al. |
| 2013/0020948 A1 | 1/2013 | Han et al. |
| 2013/0027341 A1 | 1/2013 | Mastandrea |
| 2013/0080794 A1 | 3/2013 | Hsieh |
| 2013/0127708 A1 | 5/2013 | Jung et al. |
| 2013/0165813 A1 | 6/2013 | Chang et al. |
| 2013/0191741 A1 | 7/2013 | Dickinson et al. |
| 2013/0198694 A1 | 8/2013 | Rahman et al. |
| 2013/0265229 A1 | 10/2013 | Forutanpour et al. |
| 2013/0265437 A1 | 10/2013 | Thörn et al. |
| 2013/0271292 A1 | 10/2013 | McDermott |
| 2013/0312256 A1 | 11/2013 | Wesselmann et al. |
| 2013/0317648 A1 | 11/2013 | Assad |
| 2013/0332196 A1 | 12/2013 | Pinsker |
| 2014/0020945 A1 | 1/2014 | Hurwitz et al. |
| 2014/0028539 A1 | 1/2014 | Newham et al. |
| 2014/0028546 A1 | 1/2014 | Jeon et al. |
| 2014/0045547 A1 | 2/2014 | Singamsetty et al. |
| 2014/0049417 A1 | 2/2014 | Abdurrahman et al. |
| 2014/0094675 A1 | 4/2014 | Luna et al. |
| 2014/0121471 A1 | 5/2014 | Walker |
| 2014/0122958 A1 | 5/2014 | Greenebrg et al. |
| 2014/0157168 A1 | 6/2014 | Albouyeh et al. |
| 2014/0194062 A1 | 7/2014 | Palin et al. |
| 2014/0198034 A1 | 7/2014 | Bailey et al. |
| 2014/0198035 A1 | 7/2014 | Bailey et al. |
| 2014/0236031 A1 | 8/2014 | Banet et al. |
| 2014/0240103 A1 | 8/2014 | Lake et al. |
| 2014/0249397 A1 | 9/2014 | Lake et al. |
| 2014/0257141 A1 | 9/2014 | Giuffrida et al. |
| 2014/0285326 A1 | 9/2014 | Luna et al. |
| 2014/0299362 A1 | 10/2014 | Park et al. |
| 2014/0334083 A1 | 11/2014 | Bailey |
| 2014/0334653 A1 | 11/2014 | Luna et al. |
| 2014/0337861 A1 | 11/2014 | Chang et al. |
| 2014/0340857 A1 | 11/2014 | Hsu et al. |
| 2014/0349257 A1 | 11/2014 | Connor |
| 2014/0354528 A1 | 12/2014 | Laughlin et al. |
| 2014/0354529 A1 | 12/2014 | Laughlin et al. |
| 2014/0364703 A1 | 12/2014 | Kim et al. |
| 2014/0375465 A1 | 12/2014 | Fenuccio et al. |
| 2015/0011857 A1 | 1/2015 | Henson et al. |
| 2015/0051470 A1 | 2/2015 | Bailey et al. |
| 2015/0057506 A1 | 2/2015 | Luna et al. |
| 2015/0057770 A1 | 2/2015 | Bailey et al. |
| 2015/0106052 A1 | 4/2015 | Balakrishnan et al. |
| 2015/0124566 A1 | 5/2015 | Lake et al. |
| 2015/0141784 A1 | 5/2015 | Morun et al. |
| 2015/0148641 A1 | 5/2015 | Morun et al. |
| 2015/0160621 A1 | 6/2015 | Yilmaz |
| 2015/0182113 A1 | 7/2015 | Utter, II |
| 2015/0182130 A1 | 7/2015 | Utter, II |
| 2015/0182163 A1 | 7/2015 | Utter |
| 2015/0182164 A1 | 7/2015 | Utter, II |
| 2015/0185838 A1 | 7/2015 | Camacho-Perez et al. |
| 2015/0186609 A1 | 7/2015 | Utter, II |
| 2015/0216475 A1 | 8/2015 | Luna et al. |
| 2015/0230756 A1 | 8/2015 | Luna et al. |
| 2015/0237716 A1 | 8/2015 | Su et al. |
| 2015/0261306 A1 | 9/2015 | Lake |
| 2015/0277575 A1 | 10/2015 | Ataee et al. |
| 2015/0296553 A1 | 10/2015 | DiFranco et al. |
| 2015/0310766 A1 | 10/2015 | Alshehri et al. |
| 2015/0325202 A1 | 11/2015 | Lake et al. |
| 2015/0370333 A1 | 12/2015 | Ataee et al. |
| 2016/0020500 A1 | 1/2016 | Matsuda |
| 2016/0150636 A1 | 5/2016 | Otsubo |
| 2016/0199699 A1 | 7/2016 | Klassen |
| 2016/0202081 A1 | 7/2016 | Debieuvre et al. |
| 2016/0246384 A1 | 8/2016 | Mullins et al. |
| 2016/0274758 A1 | 9/2016 | Bailey |
| 2016/0309249 A1 | 10/2016 | Wu et al. |
| 2016/0313899 A1 | 10/2016 | Noel |
| 2017/0127354 A1 | 5/2017 | Garland et al. |

FOREIGN PATENT DOCUMENTS

| | | |
|---|---|---|
| EP | 0 301 790 A2 | 2/1989 |
| JP | 07248873 A | 9/1995 |
| JP | 2008192004 A | 8/2008 |
| JP | 2009-50679 A | 3/2009 |
| KR | 10-2012-0094870 A | 8/2012 |
| KR | 10-2012-0097997 A | 9/2012 |
| WO | 2011/070554 A2 | 6/2011 |

OTHER PUBLICATIONS

Communication pursuant to Rule 164(1) EPC, dated Sep. 30, 2016, for corresponding EP Application No. 14753949.8, 7 pages.

Costanza et al., "EMG as a Subtle Input Interface for Mobile Computing," *Mobile HCI 2004*, LNCS 3160, edited by S. Brewster and M. Dunlop, Springer-Verlag Berlin Heidelberg, pp. 426-430, 2004.

Costanza et al., "Toward Subtle Intimate Interfaces for Mobile Devices Using an EMG Controller," CHI 2005, *Proceedings of the SIGCHI Conference on Human Factors in Computing Systems*, pp. 481-489, 2005.

Ghasemzadeh et al., "A Body Sensor Network With Electromyogram and Inertial Sensors: Multimodal Interpretation of Muscular Activities," *IEEE Transactions on Information Technology in Biomedicine*, vol. 14, No. 2, pp. 198-206, Mar. 2010.

Gourmelon et al., "Contactless sensors for Surface Electromyography," *Proceedings of the 28th IEEE EMBS Annual International Conference*, New York City, NY, Aug. 30-Sep. 3, 2006, pp. 2514-2517.

International Search Report and Written Opinion, dated Aug. 21, 2014, for International Application No. PCT/US2014/037863, 12 pages.

(56) References Cited

OTHER PUBLICATIONS

International Search Report and Written Opinion, dated Feb. 27, 2015, for International Application No. PCT/US2014/067443, 13 pages.
International Search Report and Written Opinion, dated May 16, 2014, for International Application No. PCT/US2014/017799, 11 pages.
International Search Report and Written Opinion, dated May 27, 2015, for International Application No. PCT/US2015/015675, 9 pages.
International Search Report and Written Opinion, dated Nov. 21, 2014, for International Application No. PCT/US2014/052143, 11 pages.
Janssen, "Radio Frequency (RF)" 2013, retrieved from https://web.archive.org/web/20130726153946/htttps://www.techopedia.com/definition/5083/radio-frequency-rf, retrieved on Jul. 12, 2017, 2 pages.
Merriam-Webster, "Radio Frequencies" retrieved from https://www.merriam-webster.com/table/collegiate/radiofre.htm, retrieved on Jul. 12, 2017, 2 pages.
Morris et al., "Emerging Input Technologies for Always-Available Mobile Interaction," *Foundations and Trends in Human-Computer Interaction* 4(4):245-316, 2011. (74 total pages).
Naik et al., "Real-Time Hand Gesture Identification for Human Computer Interaction Based on ICA of Surface Electromyogram," *IADIS International Conference Interfaces and Human Computer Interaction 2007*, 8 pages.
Picard et al., "Affective Wearables," *Proceedings of the IEEE $1^{st}$ International Symposium on Wearable Computers*, ISWC, Cambridge, MA, USA, Oct. 13-14, 1997, pp. 90-97.
Rekimoto, "GestureWrist and GesturePad: Unobtrusive Wearable Interaction Devices," ISWC '01 *Proceedings of the $5^{th}$ IEEE International Symposium on Wearable Computers*, 2001, 7 pages.
Saponas et al., "Making Muscle-Computer Interfaces More Practical," *CHI 2010*, Atlanta, Georgia, USA, Apr. 10-15, 2010, 4 pages.
Sato et al., "Touché: Enhancing Touch Interaction on Humans, Screens, Liquids, and Everyday Objects," *CHI '12*, May 5-10, 2012, Austin, Texas.
Ueno et al., "A Capacitive Sensor System for Measuring Laplacian Electromyogram through Cloth: A Pilot Study," *Proceedings of the 29th Annual International Conference of the IEEE EMBS*, Cité Internationale, Lyon, France, Aug. 23-26, 2007, pp. 5731-5734.
Ueno et al., "Feasibility of Capacitive Sensing of Surface Electromyographic Potential through Cloth," *Sensors and Materials* 24(6):335-346, 2012.
Xiong et al., "A Novel HCI based on EMG and IMU," *Proceedings of the 2011 IEEE International Conference on Robotics and Biomimetics*, Phuket, Thailand, Dec. 7-11, 2011, 5 pages.
Xu et al., "Hand Gesture Recognition and Virtual Game Control Based on 3D Accelerometer and EMG Sensors," *Proceedings of the 14th international conference on Intelligent user interfaces*, Sanibel Island, Florida, Feb. 8-11, 2009, pp. 401-406.
Zhang et al., "A Framework for Hand Gesture Recognition Based on Accelerometer and EMG Sensors," *IEEE Transactions on Systems, Man, and Cybernetics—Part A: Systems and Humans*, vol. 41, No. 6, pp. 1064-1076, Nov. 2011.

SYSTEMS, ARTICLES, AND METHODS FOR ELECTROMYOGRAPHY SENSORS

CROSS-REFERENCE TO RELATED APPLICATIONS

This Application is a Continuation of U.S. application Ser. No. 14/533,657, filed Nov. 25, 2014, entitled "SYSTEMS, ARTICLES, AND METHODS FOR ELECTROMYOGRAPHY SENSORS", which is a Non-Provisional of Provisional (35 USC § 119(e)) of U.S. application Ser. No. 61/909,786, filed Nov. 27, 2013, entitled "SYSTEMS, ARTICLES, AND METHODS FOR ELECTROMYOGRAPHY SENSORS". The entire contents of these applications are incorporated herein by reference in their entirety.

BACKGROUND

Technical Field

The present systems, articles, and methods generally relate to electromyography and particularly relate to capacitive electromyography sensors that resistively couple to the user's body.

Description of the Related Art

Wearable Electronic Devices

Electronic devices are commonplace throughout most of the world today. Advancements in integrated circuit technology have enabled the development of electronic devices that are sufficiently small and lightweight to be carried by the user. Such "portable" electronic devices may include on-board power supplies (such as batteries or other power storage systems) and may be designed to operate without any wire-connections to other electronic systems; however, a small and lightweight electronic device may still be considered portable even if it includes a wire-connection to another electronic system. For example, a microphone may be considered a portable electronic device whether it is operated wirelessly or through a wire-connection.

The convenience afforded by the portability of electronic devices has fostered a huge industry. Smartphones, audio players, laptop computers, tablet computers, and ebook readers are all examples of portable electronic devices. However, the convenience of being able to carry a portable electronic device has also introduced the inconvenience of having one's hand(s) encumbered by the device itself. This problem is addressed by making an electronic device not only portable, but wearable.

A wearable electronic device is any portable electronic device that a user can carry without physically grasping, clutching, or otherwise holding onto the device with their hands. For example, a wearable electronic device may be attached or coupled to the user by a strap or straps, a band or bands, a clip or clips, an adhesive, a pin and clasp, an article of clothing, tension or elastic support, an interference fit, an ergonomic form, etc. Examples of wearable electronic devices include digital wristwatches, electronic armbands, electronic rings, electronic ankle-bracelets or "anklets," head-mounted electronic display units, hearing aids, and so on.

Human-Electronics Interfaces

A wearable electronic device may provide direct functionality for a user (such as audio playback, data display, computing functions, etc.) or it may provide electronics to interact with, communicate with, or control another electronic device. For example, a wearable electronic device may include sensors that are responsive to (i.e., detect and provide one or more signal(s) in response to detecting) inputs effected by a user and transmit signals to another electronic device based on those inputs. Sensor-types and input-types may each take on a variety of forms, including but not limited to: tactile sensors (e.g., buttons, switches, touchpads, or keys) providing manual control, acoustic sensors providing voice-control, electromyography sensors providing gesture control, or accelerometers providing gesture control.

A human-computer interface ("HCI") is an example of a human-electronics interface. The present systems, articles, and methods may be applied to HCIs, but may also be applied to any other form of human-electronics interface.

Electromyography Sensors

Electromyography ("EMG") is a process for detecting and processing the electrical signals generated by muscle activity. EMG devices employ EMG sensors that are responsive to the range of electrical potentials (typically μV-mV) involved in muscle activity. EMG signals may be used in a wide variety of applications, including: medical monitoring and diagnosis, muscle rehabilitation, exercise and training, prosthetic control, and even in controlling functions of electronic devices (i.e., in human-electronics interfaces).

There are two main types of EMG sensors: intramuscular EMG sensors and surface EMG sensors. As the names suggest, intramuscular EMG sensors are designed to penetrate the skin and measure EMG signals from within the muscle tissue, while surface EMG sensors are designed to rest on an exposed surface of the skin and measure EMG signals from there. Intramuscular EMG sensor measurements can be much more precise than surface EMG sensor measurements; however, intramuscular EMG sensors must be applied by a trained professional, are obviously more invasive, and are less desirable from the patient's point of view. The use of intramuscular EMG sensors is generally limited to clinical settings.

Surface EMG sensors can be applied with ease, are much more comfortable for the patient/user, and are therefore more appropriate for non-clinical settings and uses. For example, human-electronics interfaces that employ EMG, such as those proposed in U.S. Pat No. 6,244,873 and U.S. Pat. No. 8,170,656, usually employ surface EMG sensors. Surface EMG sensors are available in two forms: resistive EMG sensors and capacitive EMG sensors. The electrode of a resistive EMG sensor is typically directly electrically coupled to the user's skin while the electrode of a capacitive EMG sensor is typically capacitively coupled to the user's skin. That is, for a resistive EMG sensor, the electrode typically comprises a plate of electrically conductive material that is in direct physical contact with the user's skin, while for a capacitive EMG sensor, the electrode typically comprises a plate of electrically conductive material that is electrically insulated from the user's skin by at least one thin intervening layer of dielectric material or cloth.

Resistive EMG sensors and capacitive EMG sensors both have relative advantages and disadvantages. For example, the resistive coupling to the skin realized by a resistive EMG sensor provides a relatively low impedance (compared to a capacitive coupling) between the skin and the sensor and this can greatly simplify the circuitry needed to amplify the detected EMG signals; however, because this resistive coupling is essentially galvanic and uninterrupted, it can also undesirably couple DC voltage to the amplification circuitry and/or result in a voltage applied to the skin of the user. Both of these effects potentially impact the quality of the EMG signals detected. On the other hand, the capacitive coupling to the skin realized by a capacitive EMG sensor galvanically isolates the amplification circuitry from the skin and thereby prevents a DC voltage from coupling to the amplification circuitry and prevents a voltage from being applied to the skin; however, this capacitive coupling provides a relatively high impedance between the skin and the sensor and this can complicate the circuitry needed to amplify the detected EMG signals (thus making the amplification circuitry more expensive). The strength of the capacitive coupling can also vary widely from user to user. Clearly, neither type of surface EMG sensor is ideal and there is a need in the art for improved surface EMG sensor designs.

BRIEF SUMMARY

An electromyography ("EMG") sensor may be summarized as including a first sensor electrode formed of an electrically conductive material; an amplifier; a first electrically conductive pathway that communicatively couples the first sensor electrode and the amplifier; a first capacitor electrically coupled in series between the first sensor electrode and the amplifier in the first electrically conductive pathway; and a first resistor electrically coupled in series between the first sensor electrode and the amplifier in the first electrically conductive pathway. The first capacitor and the first resistor may be electrically coupled in series with one another in the first electrically conductive pathway. The EMG sensor may further include: a second electrically conductive pathway that communicatively couples to ground; a third electrically conductive pathway that communicatively couples the first electrically conductive pathway and the second electrically conductive pathway; a second capacitor electrically coupled in the third electrically conductive pathway in between the first electrically conductive pathway and the second electrically conductive pathway; a fourth electrically conductive pathway that communicatively couples the first electrically conductive pathway and the second electrically conductive pathway; and a second resistor electrically coupled in the fourth electrically conductive pathway in between the first electrically conductive pathway and the second electrically conductive pathway. The EMG sensor may be a differential EMG sensor that further includes: a second sensor electrode formed of an electrically conductive material; a fifth electrically conductive pathway that communicatively couples the second sensor electrode and the amplifier; a third capacitor electrically coupled in series between the second sensor electrode and the amplifier in the fifth electrically conductive pathway; and a third resistor electrically coupled in series between the second sensor electrode and the amplifier in the fifth electrically conductive pathway. The third capacitor and the third resistor may be electrically coupled in series with one another in the fifth electrically conductive pathway. The EMG sensor may further include: a sixth electrically conductive pathway that communicatively couples the fifth electrically conductive pathway and the second electrically conductive pathway; a fourth capacitor electrically coupled in the sixth electrically conductive pathway in between the fifth electrically conductive pathway and the second electrically conductive pathway; a seventh electrically conductive pathway that communicatively couples the fifth electrically conductive pathway and the second electrically conductive pathway; and a fourth resistor electrically coupled in the seventh electrically conductive pathway in between the fifth electrically conductive pathway and the second electrically conductive pathway. The EMG sensor may further include a ground electrode formed of an electrically conductive material and communicatively coupled to the second electrically conductive pathway.

The first sensor electrode may comprise a first layer formed of a first electrically conductive material and a second layer formed of a second electrically conductive material. The first electrically conductive material may include copper. The second electrically conductive material may include at least one material selected from the group consisting of: gold, steel, stainless steel, silver, titanium, electrically conductive rubber, and electrically conductive silicone.

The EMG sensor may further include a housing, wherein the amplifier, the first electrically conductive pathway, the first capacitor, the first resistor, and the first layer of the first sensor electrode are all substantially contained within the housing, the housing including a hole, and wherein at least a portion of the second layer of the first sensor electrode extends out of the housing through the hole. The EMG sensor may further include a substrate having a first surface and a second surface, the second surface opposite the first surface across a thickness of the substrate, wherein the first sensor electrode is carried by the first surface of the substrate and the amplifier, the first capacitor, and the first resistor are all carried by the second surface of the substrate. The first electrically conductive pathway may include at least one via that extends through the substrate. The first electrically conductive pathway may include at least one electrically conductive trace carried by the second surface of the substrate. The first capacitor and the first resistor may include respective discrete electronic components.

A method of fabricating an electromyography ("EMG") sensor may be summarized as including: forming a first sensor electrode on a first surface of a substrate, wherein forming a first sensor electrode on a first surface of a substrate includes depositing at least a first layer of a first electrically conductive material on the first surface of the substrate; depositing an amplifier on a second surface of the substrate, the second surface opposite the first surface across a thickness of the substrate; depositing a first capacitor on the second surface of the substrate; depositing a first resistor on the second surface of the substrate; and forming a first electrically conductive pathway that communicatively couples the first sensor electrode and the amplifier through the first capacitor and the first resistor. Forming the first electrically conductive pathway may include forming a via through the substrate. Depositing at least a first layer of a first electrically conductive material on the first surface of the substrate may include depositing a first layer including copper on the first surface of the substrate, and forming the first sensor electrode may further include depositing a second layer of a second electrically conductive material on the first layer of the first electrically conductive material, the second electrically conductive material including a material selected from the group consisting of: gold, steel, stainless steel, silver, titanium, electrically conductive rubber, and electrically conductive silicone.

The method may further include enclosing the substrate in a housing, wherein the housing includes a hole, and wherein enclosing the substrate in a housing includes enclosing the amplifier, the first capacitor, and the first resistor in the housing and aligning the first sensor electrode with the hole, wherein at least a portion of the second layer of the second electrically conductive material protrudes out of the housing through the hole.

The method may further include forming a ground electrode on the first surface of the substrate; forming a second electrically conductive pathway that communicatively couples to the ground electrode; depositing a second capacitor on the second surface of the substrate; forming a third electrically conductive pathway that communicatively couples the first electrically conductive pathway and the second electrically conductive pathway through the second capacitor; depositing a second resistor on the second surface of the substrate; and forming a fourth electrically conductive pathway that communicatively couples the first electrically conductive pathway and the second electrically conductive pathway through the second resistor. The EMG sensor may be a differential EMG sensor, and the method may further include: forming a second sensor electrode on the first surface of the substrate; depositing a third capacitor on the second surface of the substrate; depositing a third resistor on the second surface of the substrate; and forming a fifth electrically conductive pathway that communicatively couples the second sensor electrode and the amplifier through the third capacitor and the third resistor. The method may further include: depositing a fourth capacitor on the second surface of the substrate; forming a sixth electrically conductive pathway that communicatively couples the fifth electrically conductive pathway and the second electrically conductive pathway through the fourth capacitor; depositing a fourth resistor on the second surface of the substrate; and forming a seventh electrically conductive pathway that communicatively couples the fifth electrically conductive pathway and the second electrically conductive pathway through the fourth resistor.

Depositing the amplifier on the second surface of the substrate may include soldering the amplifier on the second surface of the substrate; depositing the first capacitor on the second surface of the substrate may include soldering the first capacitor on the second surface of the substrate; and/or depositing the first resistor on the second surface of the substrate may include soldering the first resistor on the second surface of the substrate.

A wearable electromyography ("EMG") device may be summarized as including: at least one EMG sensor responsive to (i.e., to detect and provide at least one signal in response to) muscle activity corresponding to a gesture performed by a user of the wearable EMG device, wherein in response to muscle activity corresponding to a gesture performed by a user the at least one EMG sensor provides signals, and wherein the at least one EMG sensor includes: a first sensor electrode formed of an electrically conductive material; an amplifier; a first electrically conductive pathway that communicatively couples the first sensor electrode and the amplifier; a first capacitor electrically coupled in series between the first sensor electrode and the amplifier in the first electrically conductive pathway; and a first resistor electrically coupled in series between the first sensor electrode and the amplifier in the first electrically conductive pathway; a processor communicatively coupled to the at least one EMG sensor to in use process signals provided by the at least one EMG sensor; and an output terminal communicatively coupled to the processor to transmit signals output by the processor. The at least one EMG sensor may further include: a second electrically conductive pathway that communicatively couples to ground; a third electrically conductive pathway that communicatively couples the first electrically conductive pathway and the second electrically conductive pathway; a second capacitor electrically coupled in between the first electrically conductive pathway and the second electrically conductive pathway in the third electrically conductive pathway; a fourth electrically conductive pathway that communicatively couples the first electrically conductive pathway and the second electrically conductive pathway; and a second resistor electrically coupled in between the first electrically conductive pathway and the second electrically conductive pathway in the fourth electrically conductive pathway. The at least one EMG sensor may include at least one differential EMG sensor, and the at least one differential EMG sensor may further include: a second sensor electrode formed of an electrically conductive material; a fifth electrically conductive pathway that communicatively couples the second sensor electrode and the amplifier; a third capacitor electrically coupled in between the second sensor electrode and the amplifier in the fifth electrically conductive pathway; and a third resistor electrically coupled in between the second sensor electrode and the amplifier in the fifth electrically conductive pathway. The at least one EMG sensor may further include a ground electrode formed of an electrically conductive material and communicatively coupled to the second electrically conductive pathway.

The first sensor electrode of the at least one EMG sensor may comprise a first layer formed of a first electrically conductive material and a second layer formed of a second electrically conductive material. The first electrically conductive material may include copper. The second electrically conductive material may include at least one material selected from the group consisting of: gold, steel, stainless steel, silver, titanium, electrically conductive rubber, and electrically conductive silicone. The wearable EMG device may further include: at least one housing that at least partially contains the at least one EMG sensor, wherein the amplifier, the first electrically conductive pathway, the first capacitor, the first resistor, and the first layer of the first sensor electrode are all substantially contained within the at least one housing, the at least one housing including a hole, and wherein at least a portion of the second layer of the first sensor electrode extends out of the at least one housing through the hole.

A capacitive electromyography ("EMG") sensor may be summarized as including: a first sensor electrode to in use resistively couple to a user's skin, wherein the first sensor electrode includes a plate of electrically conductive material; circuitry communicatively coupled to the first sensor electrode of the capacitive EMG sensor; and a first capacitor to in use galvanically isolate the circuitry from the user's skin, the first capacitor electrically coupled in series between the first sensor electrode and the circuitry. Resistive coupling between the first sensor electrode and the user's skin may include an impedance, and the capacitive EMG sensor may further include a first resistor to in use dominate the impedance of the resistive coupling between the first sensor electrode and the user's skin, wherein the first resistor is electrically coupled in series between the first sensor electrode and the circuitry and wherein the first resistor has a magnitude of at least 1 k$\Omega$. The first resistor may have a magnitude of at least 10 k$\Omega$. The circuitry may include at least a portion of at least one circuit selected from the group consisting of: an amplification circuit, a filtering circuit, and an analog-to-digital conversion circuit. The capacitive EMG sensor may further include a ground electrode to in use resistively couple to the user's skin, wherein the ground electrode includes a plate of electrically conductive material, and wherein the ground electrode is communicatively coupled to the circuitry. The circuitry may include: a high-pass filter that includes the first capacitor and a second resistor; and a low-pass filter that includes the first resistor and a second capacitor.

The first sensor electrode may comprise: a first layer of a first electrically conductive material; and a second layer of a second electrically conductive material. The first electrically conductive material may include copper. The second electrically conductive material may include at least one material selected from the group consisting of: gold, steel, stainless steel, silver, titanium, electrically conductive rubber, and electrically conductive silicone. The capacitive EMG sensor may further include a housing, wherein the circuitry, the first capacitor, and the first layer of the first sensor electrode are all substantially contained within the housing, the housing including a hole, and wherein at least a portion of the second layer of the first sensor electrode extends out of the housing through the hole. The capacitive EMG sensor may be a differential capacitive EMG sensor that further includes: a second sensor electrode to in use resistively couple to the user's skin, wherein the second sensor electrode includes a plate of electrically conductive material; and a second capacitor to in use galvanically isolate the circuitry from the user's skin, the second capacitor electrically coupled in series between the second sensor electrode and the circuitry.

A wearable electromyography ("EMG") device may be summarized as including: at least one capacitive EMG sensor responsive to (i.e., to detect and provide at least one signal in response to detecting) muscle activity corresponding to a gesture performed by a user of the wearable EMG device, wherein in response to muscle activity corresponding to a gesture performed by a user the at least one capacitive EMG sensor provides signals, and wherein the at least one capacitive EMG sensor includes: a first sensor electrode to in use resistively couple to the user's skin, wherein the first sensor electrode includes a plate of electrically conductive material; circuitry communicatively coupled to the first sensor electrode of the capacitive EMG sensor; and a first capacitor to in use galvanically isolate the circuitry from the user's skin, the first capacitor electrically coupled in series between the first sensor electrode and the circuitry; a processor communicatively coupled to the at least one capacitive EMG sensor to in use process signals provided by the at least one capacitive EMG sensor; and an output terminal communicatively coupled to the processor to transmit signals output by the processor.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

DETAILED DESCRIPTION

Figure 1:
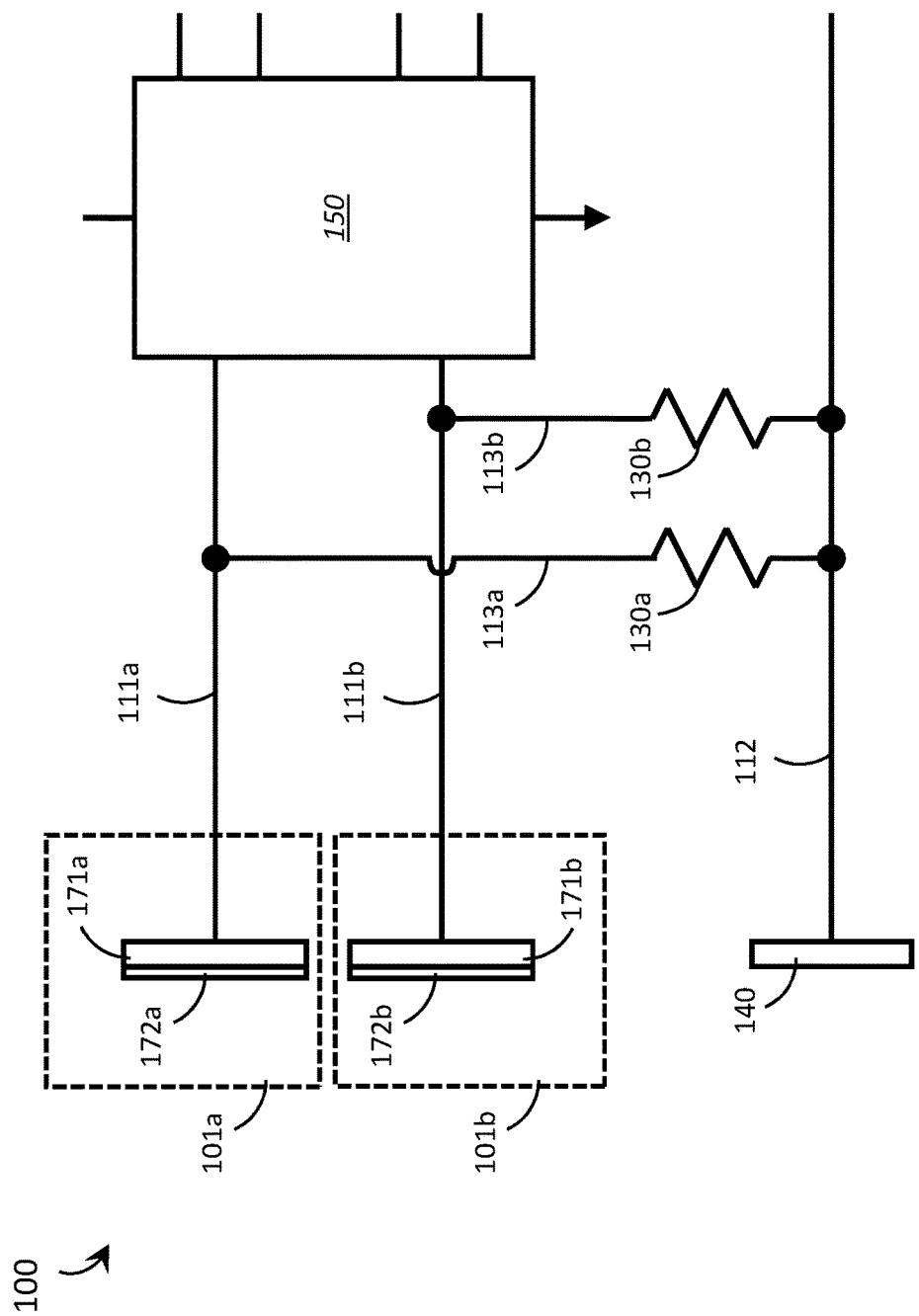
FIG. 1 is a schematic diagram of a capacitive EMG sensor that employs sensor electrodes that are configured to capacitively couple to the skin of a user.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with electric circuits, and in particular printed circuit boards, have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its broadest sense, that is as meaning "and/or" unless the content clearly dictates otherwise.

The headings and Abstract of the Disclosure provided herein are for convenience only and do not interpret the scope or meaning of the embodiments.

The various embodiments described herein provide systems, articles, and methods for surface EMG sensors that improve upon existing resistive and capacitive EMG sensor designs. The surface EMG sensors described herein may be understood as hybrid surface EMG sensors that incorporate elements from both resistive EMG sensors and capacitive EMG sensors. In particular, the present systems, articles, and methods describe capacitive EMG sensors that employ at least one sensor electrode that resistively couples to the user's body (e.g., skin) and at least one discrete component capacitor that interrupts the signal path between the at least one sensor electrode and the sensor circuitry. In this way, the capacitive element of the capacitive EMG sensor remains but is essentially moved downstream in the sensor circuit, affording many benefits discussed in detail below. An example application in a wearable EMG device that forms part of a human-electronics interface is also described.

Throughout this specification and the appended claims, the term "capacitive EMG sensor" is used to describe a surface EMG sensor in which communicative coupling between the user's body (e.g., skin) and the sensor circuitry is mediated by at least one capacitive element such that the sensor circuitry is galvanically isolated from the body of the user. In the art, this at least one capacitive element is typically realized at the sensor electrode by configuring the sensor electrode to capacitively couple to the user's skin (e.g., by coating the electrically conductive plate of the sensor electrode with a thin layer of dielectric material). In accordance with the present systems, articles, and methods, the at least one capacitive element may be moved downstream in the sensor such that the sensor electrode resistively/galvanically couples to the user's skin but at least one discrete component capacitor mediates communicative coupling between the sensor electrode and the sensor circuitry.

For comparison purposes, the elements of a capacitive EMG sensor that implements a sensor electrode that capacitively couples to the user's skin are first described.

FIG. 1 is a schematic diagram of a capacitive EMG sensor 100 that employs sensor electrodes 101a, 101b that are configured to capacitively couple to the skin of a user. Sensor 100 is a differential capacitive EMG sensor that employs two sensor electrodes 101a, 101b as described in, for example, U.S. Provisional Patent Application Ser. No. 61/771,500 (now U.S. Non-Provisional patent application Ser. No. 14/194,252) which is incorporated by reference herein in its entirety. However, a person of skill in the art will appreciate that the basic description of sensor 100 herein is also applicable to single-ended sensor systems that employ only a single sensor electrode (i.e., one of sensor electrodes 101a or 101b). Sensor electrodes 101a and 101b each comprise a respective electrically conductive plate 171a, 171b coated with a respective layer of dielectric material 172a, 172b. Sensor 100 also includes a ground electrode 140 that comprises an electrically conductive plate that is exposed (i.e., not coated with dielectric material) so that ground electrode 140 resistively couples to the user's skin as described in U.S. Provisional Patent Application Ser. No. 61/903,238 (now U.S. Non-Provisional patent application Ser. No. 14/539,773), which is incorporated herein by reference in its entirety.

Sensor 100 includes circuitry that comprises, at least: electrically conductive pathways 111a, 111b, 112, 113a, 113b; resistors 130a, 130b; and amplifier 150. First sensor electrode 101a is communicatively coupled to amplifier 150 through electrically conductive pathway 111a and to ground electrode 140 through a path that comprises electrically conductive pathway 113a, resistor 130a, and electrically conductive pathway 112. Second sensor electrode 101b is communicatively coupled to amplifier 150 through electrically conductive pathway 111b and to ground electrode 140 through a path that comprises electrically conductive pathway 113b, resistor 130b, and electrically conductive pathway 112.

Sensor 100 is a capacitive EMG sensor in the traditional sense because it implements sensor electrodes 101a, 101b that are configured to capacitively couple to the skin of the user. Amplifier 150 is galvanically isolated from the user's skin by the dielectric layers 172a, 172b that coat sensor electrodes 101a, 101b, respectively. As discussed previously, this galvanic isolation is advantageous, at least because it prevents DC voltage(s) from coupling to amplifier 150 and prevents voltage(s) from being applied to the user's skin. However, the capacitive coupling to the skin through sensor electrodes 101a, 101b introduces a relatively large impedance between the user's skin and amplifier 150. This impedance imposes stringent requirements on amplifier 150 and, ultimately, increases the cost of amplifier 150 in sensor 100. Furthermore, the magnitude of the capacitive coupling between sensor electrodes 101a, 101b and the user's skin is highly dependent on parameters such as skin conductance, skin moisture/sweat levels, hair density, and so on, all of which can vary considerably from user to user (and even in different scenarios for the same user, such as at different levels of physical activity). Thus, even though the galvanic isolation realized by dielectric layers 172a and 172b is desirable in a surface EMG sensor, capacitive coupling between sensor electrodes 101a, 101b and the user's skin has undesirable consequences. In accordance with the present systems, articles, and methods, the benefits of galvanically isolating the amplifier (e.g., 150) from the user's skin may be realized without the drawbacks of capacitively coupling the sensor electrode(s) to the user's skin by a capacitive EMG sensor design in which the capacitive interruption between the user's skin and the amplifier is moved downstream in the sensor circuit and realized by a discrete component capacitor coupled in between a resistive sensor electrode and an amplification circuit.

Figure 2:
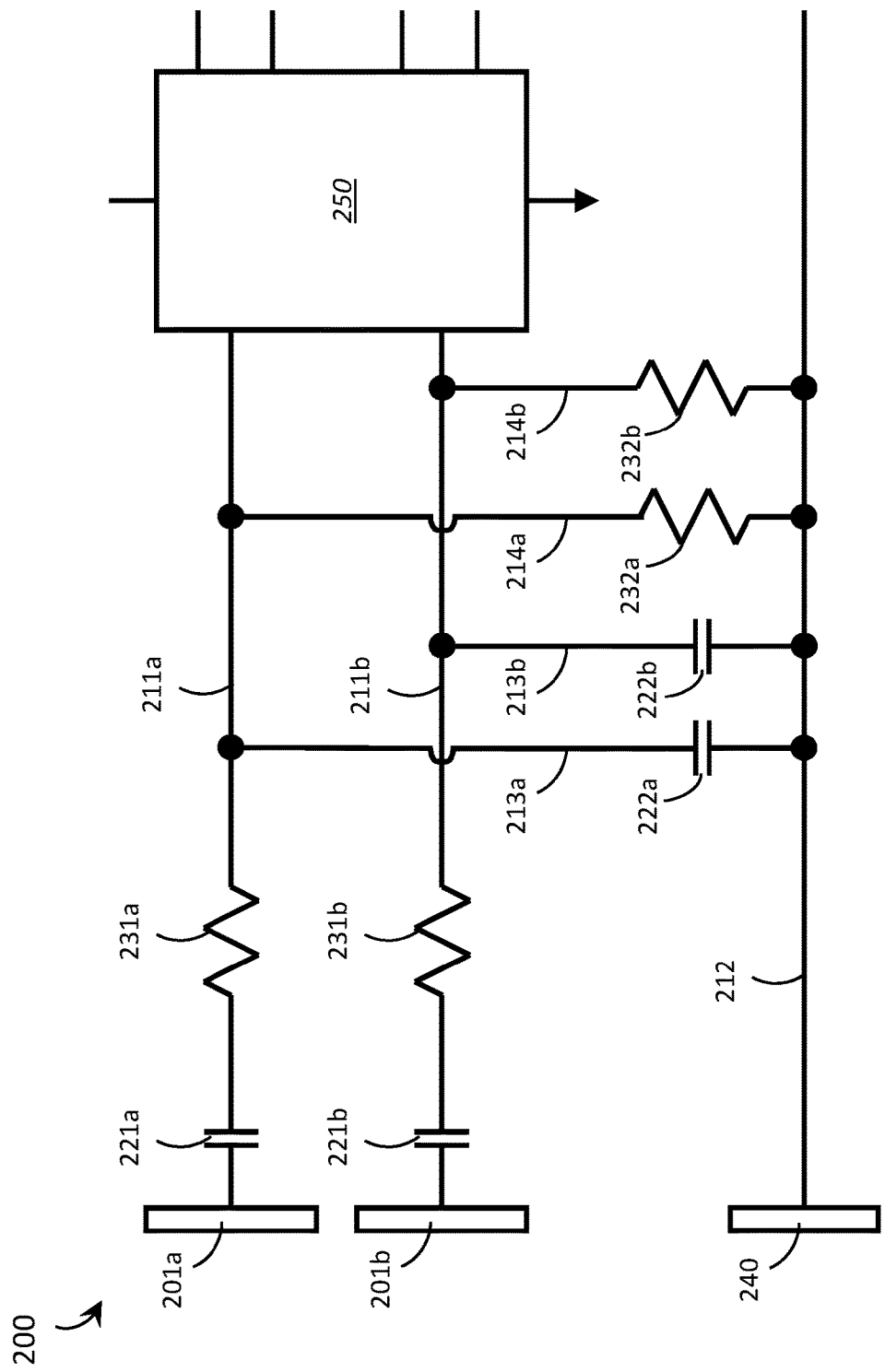
FIG. 2 is a schematic diagram of a capacitive EMG sensor employing sensor electrodes that are adapted to, in use, resistively couple to the skin of a user in accordance with the present systems, articles, and methods.

FIG. 2 is a schematic diagram of a capacitive EMG sensor 200 employing sensor electrodes 201a, 201b that are adapted to, in use, resistively couple to the body (e.g., skin) of a user in accordance with the present systems, articles, and methods. Each of sensor electrodes 201a and 201b comprises a respective plate of electrically conductive material, but unlike electrodes 101a and 101b from sensor 100, electrodes 201a and 201b are not coated with dielectric material. Instead, each of electrodes 201a and 201b includes a respective bare/exposed electrically conductive surface to directly physically contact the user's skin during use. Thus, capacitive EMG sensor 200 implements sensor electrodes 201a, 201b that resemble the sensor electrodes that would typically be found in a resistive EMG sensor. However, in accordance with the present systems, articles, and methods, sensor 200 is still a capacitive EMG sensor because sensor 200 includes discrete component capacitors 221a and 221b that galvanically isolate the rest of the sensor circuitry from the user's body (e.g., skin).

Sensor 200 is illustrated as a differential capacitive EMG sensor that employs a first sensor electrode 201a and a second sensor electrode 201b, though a person of skill in the art will appreciate that the description of sensor 200 herein is also applicable to single-ended sensor systems that employ only a single sensor electrode (i.e., one of sensor electrodes 201a or 201b).

Sensor 200 includes an amplification circuit (i.e., an amplifier) 250. First sensor electrode 201a is communicatively coupled to amplifier 250 by a first electrically conductive pathway 211a. A first capacitor 221a is electrically coupled in series between first sensor electrode 201a and amplifier 250 in first electrically conductive pathway 211a. First capacitor 221a galvanically isolates amplifier 250 from the user's body (e.g., skin) and thereby affords some of the benefits typically associated with a capacitive EMG sensor (i.e., capacitor 221a prevents DC voltage(s) from coupling to amplifier 250 and prevents voltage(s) from being applied to the user's skin). While a traditional capacitive EMG sensor achieves this galvanic isolation by capacitively coupling to the user's skin at the sensor electrode (e.g., as per sensor electrode 101a from sensor 100), in sensor 200 electrode 201a is resistively coupled to the user's skin and galvanic isolation is moved downstream to discrete component capacitor 221a. As previously described, resistive coupling to the user's skin as per electrode 201a from sensor 200 provides a lower impedance between the user's skin and amplifier 250 than capacitive coupling to the user's skin as in electrode 101a from sensor 100, and this lower impedance simplifies and lowers the cost of amplifier 250 in sensor 200 compared to amplifier 150 in sensor 100. Furthermore, because capacitor 221a is a discrete component, the magnitude of its capacitance can be selected and will remain essentially constant from user to user, regardless of variations such as skin conductance, moisture/sweat levels, hair density, and so on. An example implementation may employ, as capacitors 221a (and similarly as capacitor 221b), a discrete component capacitor having a magnitude of about 100 nF. Typical capacitive coupling between a dielectric-coated cEMG sensor and a user's skin is significantly less than this, thus 100 nF may dominate the range of variations in skin:electrode capacitance typically seen in cEMG across different users and/or use conditions. The incorporation of a discrete component capacitor 221a in lieu of condition-dependent capacitive coupling between the electrode and the user's skin is very easy and inexpensive to manufacture and provides an essentially fixed capacitance to which the rest of the sensor circuitry may be tuned for improved performance.

In addition to first capacitor 221a, sensor 200 also includes a first resistor 231a that is electrically coupled in series between first sensor electrode 201a and amplifier 250 in first electrically conductive pathway 211a. Similar to first capacitor 221a, first resistor 231a may be a discrete electronic component with a magnitude that can be selected, accurately embodied, and held substantially constant during use. In the illustrated example of FIG. 2, first capacitor 221a and first resistor 231a are electrically coupled in series with one another in first electrically conductive pathway 211a. First resistor 231a is included, at least in part, to dominate the impedance between electrode 201a and the user's skin such that variations in the impedance between electrode 201a and the user's skin due to fluctuations in skin and/or environmental conditions (e.g., skin conductance, moisture/sweat levels, hair density, etc.) are rendered essentially negligible. For example, fluctuations in skin and/or environmental conditions may cause the impedance between electrode 201a and the user's skin to vary by a magnitude of on the order of 1Ω, 10Ω, 100Ω, or 1000Ω, but first resistor 231a may be selected to have a resistance of on the order of at least 1 kΩ, at least 10 kΩ, at least 100 kΩ, or more such that the impedance of first resistor 231a dominates the impedance (and, more specifically, dominates variations in the impedance) between sensor electrode 201a and the user's skin. The sensor circuitry, including amplifier 250, may be tuned to accommodate the relatively large impedance of first resistor 231a such that the relatively small variations in the impedance between sensor electrode 201a and the user's skin from user to user (and/or under different use conditions for the same user) have a diminished effect on the performance of sensor 200. First resistor 231a also serves to limit current into amplifier 250 and thereby improves the ESD protection of amplifier 250.

The amplifier(s) used in the capacitive EMG sensors described herein may include one or more of various types of amplifier(s), including one or more instrumentation amplifier(s) and/or one or more single or dual operational amplifier(s), depending, for example, on whether the EMG sensor is single-ended or differential. As sensor 200 is differential, amplifier 250 may include a dual operational amplifier (e.g., a "two-op-amp instrumentation amplifier") such as the MAX9916 or the MAX9917, both available from Maxim Integrated, or any of various other amplifier configurations, including but not limited to amplifiers embodied in integrated circuits. A person of skill in the art will appreciate that the output(s) and/or some of the inputs of amplifier 250 may be connected through various resistor configurations for at least the purpose of determining the gain of amplifier 250.

Sensor 200 includes a second electrically conductive pathway 212 that communicatively couples to ground through a ground electrode 240. Ground electrode 240 comprises a plate of electrically conductive material that resistively couples to the user's skin. As sensor 200 is differential, ground electrode 240 may not necessarily be used as a reference potential but may primarily provide a path for electrical currents to return to the user's body (e.g., skin). Using second electrically conductive pathway 212, together with first capacitor 221a and first resistor 231a, circuitry connected to first sensor electrode 201a also includes both a low-pass filtering configuration and a high-pass filtering configuration "in front of" or upstream of amplifier 250 in a direction in which signals pass. Specifically, sensor 200 includes a third electrically conductive pathway 213a that communicatively couples first electrically conductive pathway 211a and second electrically conductive pathway 212. Third electrically conductive pathway 213a includes a second capacitor 222a electrically coupled in between first electrically conductive pathway 211a and second electrically conductive pathway 212. The configuration of first resistor 231a and second capacitor 222a (with respect to sensor electrode 201a, amplifier 250, and ground electrode 240) forms a low-pass filtering circuit. As an example, when first resistor 231a has a magnitude of about 100 kΩ, second capacitor 222a may have a magnitude of about 10 pF in order to provide desirable low-pass filtering performance. Similarly, sensor 200 includes a fourth electrically conductive pathway 214a that communicatively couples first electrically conductive pathway 211a and second electrically conductive pathway 212. Fourth electrically conductive pathway 214a includes a second resistor 232a electrically coupled in between first electrically conductive pathway 211a and second electrically conductive pathway 212. The configuration of first capacitor 221a and second resistor 232a (with respect to sensor electrode 201a, amplifier 250, and ground electrode 240) forms a high-pass filtering circuit.

In comparing sensor 200 from FIG. 2 to sensor 100 from FIG. 1, second resistor 232a in sensor 200 is similar in position and function to resistor 130a in sensor 100. The magnitude of a resistor in this position (i.e., the magnitude of second resistor 232a in sensor 200 or resistor 130a in sensor 100) directly influences the filtering performance of the corresponding high-pass filter; however, as the magnitude of a resistor in this position increases, the stability of the circuit may degrade and more noise may appear. This introduces a further benefit of first capacitor 221a in sensor 200: first capacitor 221a compensates for a decrease in the magnitude of second resistor 232a and thereby allows a lower-magnitude resistor to be used for second resistor 232a in sensor 200 compared to resistor 130a in sensor 100. The lower magnitude of second resistor 232a in sensor 200 compared to resistor 130a in sensor 100 results in both reduced noise and enhanced stability in sensor 200 compared to sensor 100. As an example, second resistor 232a may have a magnitude of about 10 MΩ or less (e.g., about 1 MΩ) and first capacitor 221a may have a magnitude of about 100 nF.

As previously described, the illustrated example in FIG. 2 of capacitive EMG sensor 200 is a differential capacitive EMG sensor. To this end, sensor 200 includes: a second sensor electrode 201b that is substantially similar to first sensor electrode 201a; a fifth electrically conductive pathway 211b (analogous to first electrically conductive pathway 211a) that communicatively couples second sensor electrode 201b to amplifier 250; a third capacitor 221b (analogous to first capacitor 221a) electrically coupled in series between second sensor electrode 201b and amplifier 250 in fifth electrically conductive pathway 211b; and a third resistor 231b (analogous to first resistor 231a) electrically coupled in series between second sensor electrode 201b and amplifier 250 in fifth electrically conductive pathway 211b. In the illustrated example of FIG. 2, third capacitor 221b and third resistor 231b are electrically coupled in series with one another in fifth electrically conductive pathway 211b. Third capacitor 221b may be substantially similar to first capacitor 221a and third resistor 231b may be substantially similar to first resistor 231a. Sensor 200 also includes: a sixth electrically conductive pathway 213b (analogous to third electrically conductive pathway 213a) that communicatively couples fifth electrically conductive pathway 211b and second electrically conductive pathway 212; a fourth capacitor 222b (analogous to third capacitor 222a) electrically coupled in sixth electrically conductive pathway 213b in between fifth electrically conductive pathway 211b and second electrically conductive pathway 212; a seventh electrically conductive pathway 214b (analogous to fourth electrically conductive pathway 214a) that communicatively couples fifth electrically conductive pathway 211b and second electrically conductive pathway 212; and a fourth resistor 232b (analogous to second resistor 232a) electrically coupled in seventh electrically conductive pathway 214b in between fifth electrically conductive pathway 211b and second electrically conductive pathway 212. Third capacitor 221b and fourth resistor 232b form a high-pass filter configuration with respect to sensor electrode 201b, amplifier 250, and ground electrode 240 while third resistor 231b and fourth capacitor 222b form a low-pass filter configuration with respect to sensor electrode 201b, amplifier 250, and ground electrode 240. Fourth capacitor 222b may be substantially similar to second capacitor 222a and fourth resistor 232b may be substantially similar to second resistor 232a.

The various examples of capacitive EMG sensors described herein, including sensor 200 from FIG. 2, may be formed as a printed circuit board, formed as an integrated circuit, or otherwise carried by a substrate. In this case, one or more electrically conductive pathways (e.g., electrically conductive pathways 211a, 211b, 212, 213a, 213b, 214a, and/or 214b) may be embodied by one or more electrically conductive trace(s) carried by a substrate and formed using one or more lithography process(es).

Figure 3:
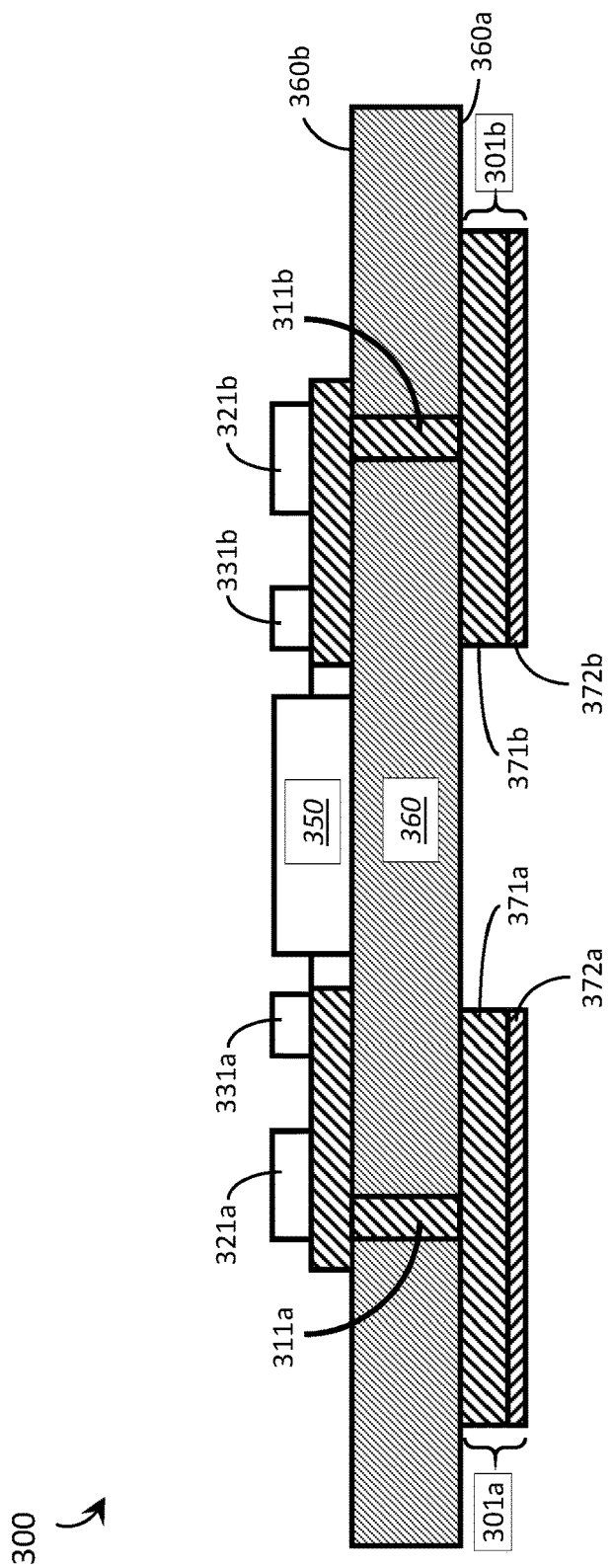
FIG. 3 is a cross sectional view of a capacitive EMG sensor that resistively couples to the user's skin in accordance with the present systems, articles, and methods.

FIG. 3 is a cross sectional view of a capacitive EMG sensor 300 that resistively couples to the user's skin in accordance with the present systems, articles, and methods. Sensor 300 is an example of a physical embodiment of the schematic diagram for sensor 200 shown in FIG. 2. Sensor 300 includes elements of sensor 200 and, in general, the descriptions of the elements of sensor 200 apply to the analogous elements in sensor 300 and vice versa.

Sensor 300 includes a substrate 360 formed of an insulating material (e.g., FR-4) and having a first surface 360a and a second surface 360b. Second surface 360b is opposite first surface 360a across a thickness of substrate 360. Sensor 300 is a differential EMG sensor comprising two sensor electrodes 301a, 301b (analogous to sensor electrodes 201a, 201b of sensor 200), both carried by first surface 360a of substrate 360. The circuitry that comprises the other elements of sensor 300 (e.g., an amplifier 350 analogous to amplifier 250 of sensor 200, capacitors 321a, 321b analogous to capacitors 221a, 221b of sensor 200, and resistors 331a, 331b analogous to resistors 231a, 231b of sensor 200) is carried by second surface 360b of substrate 360 and communicatively coupled to electrodes 301a, 301b by electrically conductive pathways 311a, 311b (analogous to electrically conductive pathways 211a, 211b of sensor 200), which include via portions that extend through the thickness of substrate 360 and electrically conductive trace portions that are carried by second surface 360b of substrate 360.

Throughout this specification and the appended claims, the terms "carries" and "carried by" are generally used to describe a spatial relationship in which a first layer/component is positioned proximate and physically coupled to a surface of a second layer/component, either directly or through one or more intervening layers/components. For example, electrode 301a is carried by first surface 360a of substrate 360 and amplifier 350 is carried by second surface 360b of substrate 360. Amplifier 350 is directly carried by second surface 360b of substrate 360 because there are no intervening layers/components that mediate the physical coupling between amplifier 350 and second surface 360b of substrate 360; however, amplifier 350 would still be considered "carried by" second surface 360b of substrate 360 even if the physical coupling between amplifier 350 and second surface 360b of substrate 360 was mediated by at least one intervening layer/component. The terms "carries" and "carried by" are not intended to denote a particular orientation with respect to top and bottom and/or left and right.

Each resistive sensor electrode of the capacitive EMG sensors described herein (e.g., electrodes 301a, 301b of sensor 300) comprises a respective electrically conductive plate that physically and electrically (i.e., galvanically/resistively) couples to the user's skin during use. For each such sensor electrode, the electrically conductive plate may be formed of, for example, a material that includes copper (such as pure elemental copper or a copper alloy), deposited and etched in accordance with established lithography techniques. While copper is an excellent material from which to form sensor electrodes 301a, 301b from a manufacturing point of view (because lithography techniques for processing copper are very well established in the art), an exposed surface of pure copper will ultimately form an insulating oxide layer and/or react with the skin of a user in other undesirable ways. This effect may be acceptable for traditional capacitive sensor electrodes that capacitively couple to the user because, as described previously, such electrodes are typically coated with an insulating dielectric layer anyway. However, the formation of such an insulating layer can undesirably effect the operation of a sensor electrode that resistively couples to the user's skin. In some cases, a user's skin may even react with copper, resulting in a rash or other discomfort for the user. For at least these reasons, in accordance with the present systems, articles, and methods it can be advantageous to form each of sensor electrodes 301a, 301b (and likewise electrodes 201a and 201b of FIG. 2) as a respective multilayer (e.g., bi-layer) structure comprising a first layer 371a, 371b formed of a first electrically conductive material (e.g., copper or a material including copper) and at least a second layer 372a, 372b formed of a second electrically conductive material. In accordance with the present systems, articles, and methods, the second electrically conductive material may be an inert, non-reactive, and/or biocompatible material. For example, the second electrically conductive material may include: gold, steel (e.g., a stainless steel such as a 316 stainless steel or a low-nickel stainless steel to mitigate dermatological nickel allergies, such as 430 stainless steel), silver, titanium, electrically conductive rubber, and/or electrically conductive silicone.

The use of multilayer (e.g., bi-layer) structures for sensor electrodes 301a, 301b is advantageous because it enables the first layer 371a, 371b to be formed of copper using established lithography techniques and the second layer 372a, 372b to be subsequently applied in order to protect the copper from exposure to the user/environment and to protect the user from exposure to the copper. Furthermore, an EMG sensor (e.g., sensor 300) may be packaged in a housing for both protective and aesthetic purposes, and a second layer 372a, 372b of electrically conductive material may be used to effectively increase the thickness of sensor electrodes 301a, 301b such that they protrude outwards from the housing to resistively couple to the user's skin during use.

Figure 4:
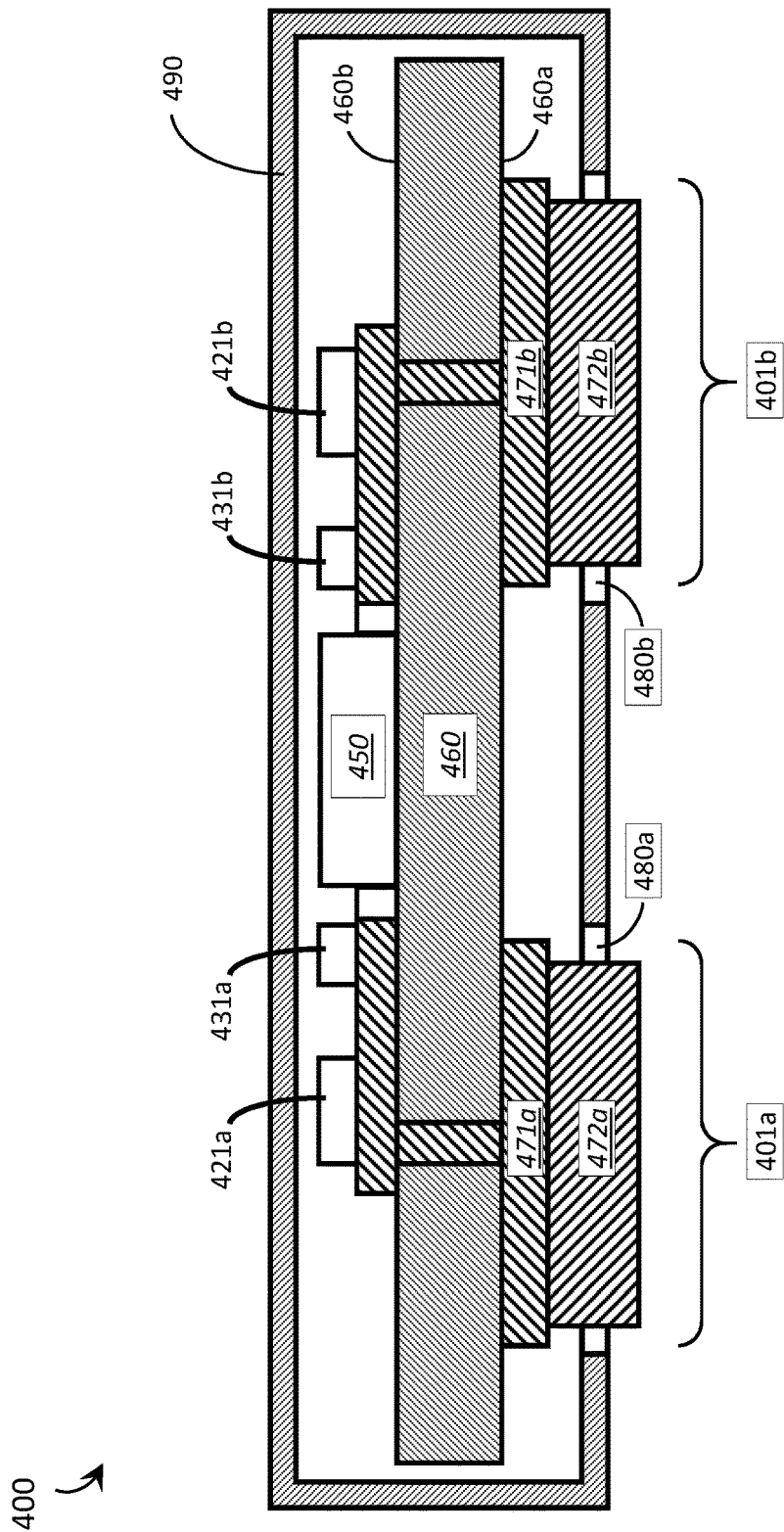
FIG. 4 is a cross sectional view of a capacitive EMG sensor packaged in a housing and employing bi-layer sensor electrodes that protrude from the housing in order to physically contact and electrically couple to a user's skin in accordance with the present systems, articles, and methods.

FIG. 4 is a cross sectional view of a capacitive EMG sensor 400 packaged in a housing 490 and employing bi-layer sensor electrodes 401a, 401b that protrude from the housing in order to physically contact and electrically (i.e., resistively/galvanically) couple to a user's skin in accordance with the present systems, articles, and methods. Sensor 400 is substantially similar to sensor 300 from FIG. 3 and includes the same or similar elements (e.g., a substrate 460 having a first surface 460a and a second surface 460b, where first surface 460a carries first and second sensor electrodes 401a, 401b and second surface 460b carries an amplifier 450, first and second capacitors 421a, 421b, first and second resistors 431a, 431b, etc.), all at least partially contained within the inner volume of a housing 490. Housing 490 may be formed of substantially rigid material. Throughout this specification and the appended claims, the term "rigid" as in, for example, "substantially rigid material," is used to describe a material that has an inherent tendency to maintain or restore its shape and resist malformation/deformation under, for example, the moderate stresses and strains typically encountered by a wearable electronic device.

Bi-layer sensor electrodes 401a, 401b are similar to bi-layer sensor electrodes 301a, 301b of sensor 300 in that they each comprise a respective first layer 471a, 471b formed of a first electrically conductive material (e.g., copper, or a material including copper) and a respective second layer 472a, 472b formed of a second electrically conductive material (e.g., gold, steel, stainless steel, conductive rubber, etc.); however, in sensor 400 the respective second layer 472a, 472b of each of electrodes 401a, 401b is substantially thicker than the respective first layer 471a, 471b of each of electrodes 401a, 401b. At least two holes 480a, 480b in housing 490 provide access to the inner volume of housing 490, and the thickness of second layers 472a, 472b of electrodes 401a, 401b (respectively) is sufficient such that at least respective portions of second layers 472a, 472b protrude out of housing 490 through holes 480a, 480b. More specifically, first sensor electrode 401a includes a first layer 471a and a second layer 472a, housing 490 includes a first hole 480a, and at least a portion of second layer 472a of first sensor electrode 401a extends out of housing 490 through first hole 480a. Likewise, second sensor electrode 401b includes a first layer 471b and a second layer 472b, housing 490 includes a second hole 480b, and at least a portion of second layer 472b of second sensor electrode 401b extends out of housing 490 through second hole 480b. In this way, housing 490 protects sensor 400 from the elements and affords opportunities to enhance aesthetic appeal, while the protruding portions of second layers 472a, 472b of sensor electrodes 401a, 401b are still able to resistively couple to the skin of the user during use. Housing 490 also helps to electrically insulate electrodes 401a, 401b from one another. In some applications, it can be advantageous to seal any gap between the perimeter of first hole 480a and the protruding portion of second layer 472a of first electrode 401a (using, e.g., a gasket, an epoxy or other sealant or, in the case of electrically conductive rubber or electrically conductive silicone as the material forming second layer 472a of first electrode 401a, a tight interference fit between the perimeter of first hole 480a and the protruding portion of second layer 472a of first electrode 401a) to prevent moisture or contaminants from entering housing 490. Likewise, it can be advantageous to seal any gap between the perimeter of second hole 480b and the protruding portion of second layer 472b of second electrode 401b.

As previously described, the various embodiments of capacitive EMG sensors described herein may include at least one ground electrode. For example, sensor 200 from FIG. 2 depicts ground electrode 240. Sensor 300 from FIG. 3 and sensor 400 from FIG. 4 each do not illustrate a ground electrode for two reasons: a) to reduce clutter; and b) because in various embodiments, a ground electrode may or may not be carried by the same substrate as the sensor electrode(s). Sensor electrodes (such as electrodes 201a, 201b, 301a, 301b, and 401a, 401b) are advantageously positioned near muscle groups in order to detect EMG signals therefrom, but in some applications it is advantageous for ground electrodes (such as electrode 240) to be positioned distant from the sensor electrodes and/or near bone instead of near muscle groups. For this reason, one or more ground electrode(s) may, in some applications, be separate from the substrate which carries the sensor electrodes but still communicatively coupled to the sensor circuitry by one or more electrically conductive pathways (e.g., electrical wires). However, in some applications one or more ground electrode(s) may be carried by the same substrate that carries the sensor electrodes, at least in part because doing so greatly simplifies the design and manufacture of the EMG sensor. For example, sensor 300 from FIG. 3 may further include a ground electrode carried by first surface 360a of substrate 360 and/or sensor 400 from FIG. 4 may further include a ground electrode carried by first surface 460a of substrate 460. In either case, the ground electrode may comprise a first layer formed of a first electrically conductive material (e.g., copper, or a material including copper) and a second layer formed of a second electrically conductive material (e.g., gold, steel, stainless steel, electrically conductive rubber, etc.). In applications that employ a housing, such as housing 490 of sensor 400, the housing may include a hole (e.g., a third hole) and at least a portion of the second layer of the ground electrode may protrude through the hole to physically contact and electrically (i.e., resistively/galvanically) couple to the skin of the user during use.

In accordance with the present systems, articles, and methods, multilayer (e.g., bi-layer) electrodes, including multilayer sensor electrodes and/or multilayer ground electrodes, may be formed by, for example: electroplating a second layer of electrically conductive material on a first layer of electrically conductive material; depositing a second layer of electrically conductive material on a first layer of electrically conductive material using deposition or growth techniques such as chemical vapor deposition, physical vapor deposition thermal oxidation, or epitaxy; adhering a second layer of electrically conductive material to a first layer of electrically conductive material using, for example, an electrically conductive epoxy or an electrically conductive solder; pressing a second layer of electrically conductive material against a first layer of electrically conductive material using, for example, an interference fit, one or more spring(s), or one or more elastic band(s); or otherwise generally bonding a second electrically conductive material to a first electrically conductive material in such a way that the second electrically conductive material is electrically coupled to the first electrically coupled material.

Figure 5:
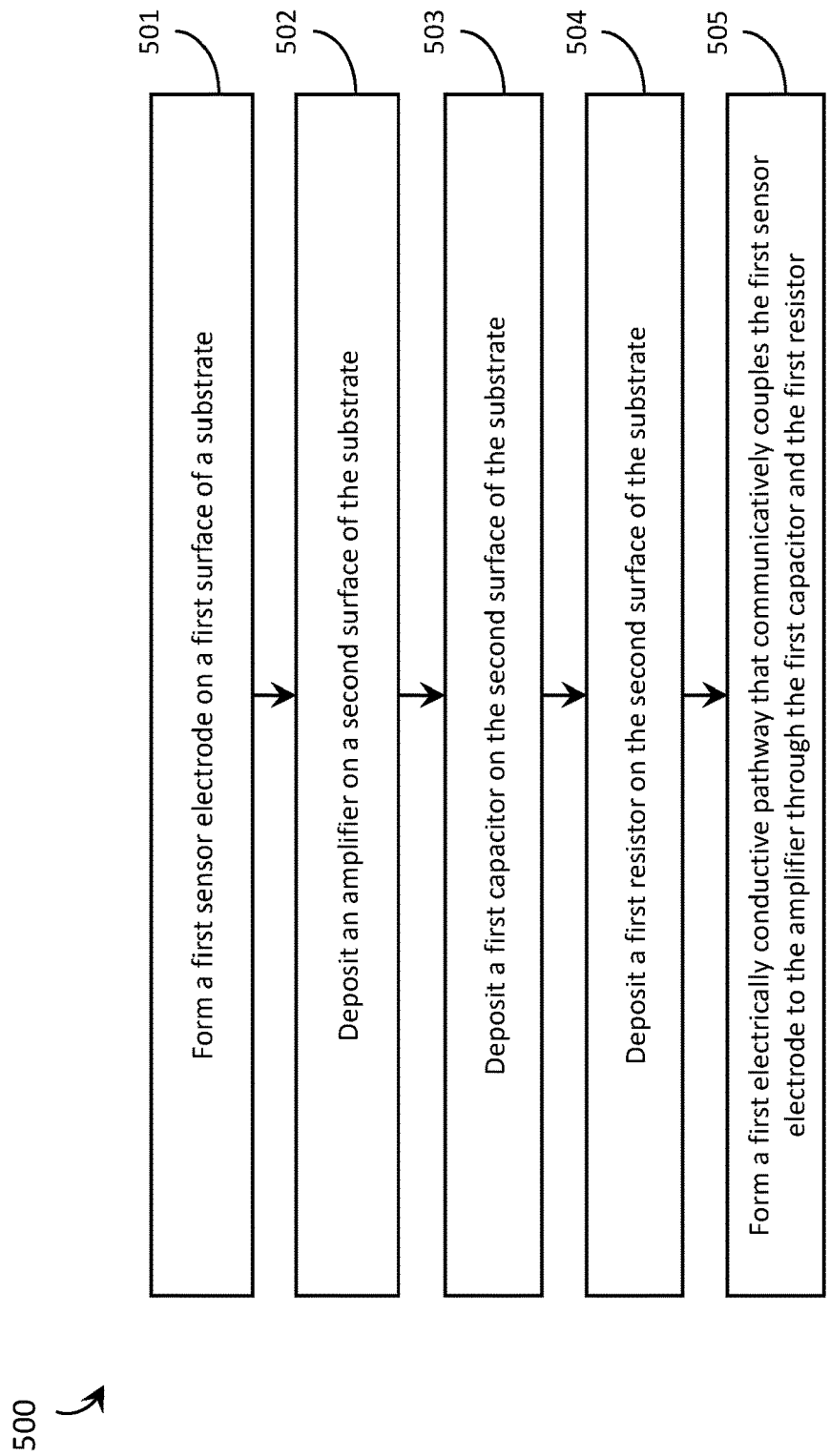
FIG. 5 is a flow-diagram of a method of fabricating an EMG sensor in accordance with the present systems, articles, and methods.

FIG. 5 is a flow-diagram of a method 500 of fabricating an EMG sensor in accordance with the present systems, articles, and methods. Method 500 includes five acts 501, 502, 503, 504, and 505, though those of skill in the art will appreciate that in alternative embodiments certain acts may be omitted and/or additional acts may be added. Those of skill in the art will also appreciate that the illustrated order of the acts is shown for exemplary purposes only and may change in alternative embodiments.

At 501, a first sensor electrode is formed on a first surface of a substrate. The first sensor electrode may comprise an electrically conductive plate such as for example electrode 301a of sensor 300 or electrode 401a of sensor 400, formed using, as an example, lithography techniques. The first sensor electrode may include a single layer of electrically conductive material or multiple (i.e., at least two) layers of one or more electrically conductive material(s). Forming the first sensor electrode may therefore include depositing at least a first layer of a first electrically conductive material (e.g., copper) on the first surface of the substrate. Where, in accordance with the present systems, articles, and methods, it is desirable for the first sensor electrode to comprise multiple layers, forming the first sensor electrode may further include depositing a second layer of a second electrically conductive material (e.g., gold, steel, stainless steel, electrically conductive rubber, etc.) on the first layer of the first electrically conductive material (either directly by, for example, a plating process or indirectly by, for example, employing an intervening adhesive layer such as an electrically conductive epoxy or an electrically conductive solder).

At 502, an amplifier (e.g., amplifier 250 of sensor 200, amplifier 350 of sensor 300, or amplifier 450 of sensor 400) is deposited on a second surface of the substrate. The amplifier may include an amplification circuit and/or one or more discrete electronic component amplifier(s), such as for example on or more operational amplifier(s), differential amplifier(s), and/or instrumentation amplifier(s). Depositing the amplifier on the second surface of the substrate may include soldering a discrete component amplifier to one or more electrically conductive trace(s) and/or bonding pad(s) carried by the second surface of the substrate (i.e., soldering the amplifier on the second surface of the substrate using, for example, a surface-mount technology, or "SMT," process).

At 503, a first capacitor (e.g., capacitor 221a of sensor 200, capacitor 321a of sensor 300, or capacitor 421a of sensor 400) is deposited on the second surface of the substrate. The first capacitor may include a discrete electronic component capacitor and depositing the first capacitor on the second surface of the substrate may include soldering the first capacitor to one or more electrically conductive trace(s) and/or bonding pad(s) carried by the second surface of the substrate (i.e., soldering the first capacitor on the second surface of the substrate using, for example, a SMT process).

At 504, a first resistor (e.g., resistor 231a of sensor 200, resistor 331a of sensor 300, or resistor 431a of sensor 400) is deposited on the second surface of the substrate. The first resistor may include a discrete electronic component resistor and depositing the first resistor on the second surface of the substrate may include soldering the first resistor to one or more electrically conductive trace(s) and/or bonding pad(s) carried by the second surface of the substrate (i.e., soldering the first resistor on the second surface of the substrate using, for example, a SMT process).

As described previously, a person of skill in the art will appreciate that the order of the acts in method 500, and in particular the order of acts 501, 502, 503, and 504, is provided as an example only and in practice acts 501, 502, 503, and 504 may be carried out in virtually any order or combination, and any/all of acts 501, 502, 503, and 504 may be carried out substantially concurrently or even simultaneously (in, for example, an SMT process).

At 505, a first electrically conductive pathway (e.g., pathway 211a of sensor 200 or pathway 311a of sensor 300) that communicatively couples the first sensor electrode to the amplifier through the first capacitor and the first resistor is formed. The first electrically conductive pathway may include one or more section(s) of electrically conductive trace carried by the second surface of the substrate and at least one via that electrically couples at least one of the one or more section(s) of electrically conductive trace to the first sensor electrode carried by the first surface of the substrate. Thus, forming the first electrically conductive pathway may employ established lithography techniques to form the one or more section(s) of electrically conductive trace and to form a via through the substrate.

As previously described, the EMG sensor may include or otherwise be packaged in a housing, such as housing 490 of sensor 400. In this case, method 500 may be extended to include enclosing the substrate in a housing. Enclosing the substrate in the housing includes enclosing the amplifier, the first capacitor, and the first resistor in the housing. The housing may include a hole providing access to the inner volume thereof, and enclosing the substrate in the housing may include aligning the first sensor electrode with the hole so that at least a portion of the first senor electrode protrudes out of the housing through the hole. For implementations in which the first sensor electrode comprises a first layer and a second layer, aligning the first sensor electrode with the hole may include aligning the first sensor electrode with the hole so that at least a portion of the second layer protrudes out of the housing through the hole.

As previously described, the EMG sensor may include a ground electrode. For example, sensor 200 from FIG. 2 includes ground electrode 240. In order to include a ground electrode (240) and associated circuitry in an EMG sensor, method 500 may be extended to include: forming the ground electrode (240) on the first surface of the substrate; forming a second electrically conductive pathway (212) that communicatively couples to the ground electrode (240); depositing a second capacitor (222a) on the second surface of the substrate; forming a third electrically conductive pathway (213a) that communicatively couples the first electrically conductive pathway (211a) and the second electrically conductive pathway (212) through the second capacitor (222a); depositing a second resistor (232a) on the second surface of the substrate; and forming a fourth electrically conductive pathway (214a) that communicatively couples the first electrically conductive pathway (211a) and the second electrically conductive pathway (212) through the second resistor (232a). Forming the ground electrode and the second, third, and fourth electrically conductive pathways may employ established lithography processes. Depositing the second capacitor and the second resistor may involve soldering discrete circuit components on the substrate (e.g., using a SMT process).

With or without a ground electrode (240), the EMG sensor may be differential. For example, sensor 200 from FIG. 2 includes second sensor electrode 201b. In order to include a second sensor electrode (201b) and associated circuitry in an EMG sensor, method 500 may be extended to include: forming a second sensor electrode (201b) on the first surface of the substrate; depositing a third capacitor (221b) on the second surface of the substrate; depositing a third resistor (231b) on the second surface of the substrate; and forming a fifth electrically conductive pathway (211b) that communicatively couples the second sensor electrode (201b) and the amplifier (250) through the third capacitor (221b) and the third resistor (231b). Forming the second sensor electrode and the fifth electrically conductive pathway may employ established lithography processes. Depositing the third capacitor and the third resistor may involve soldering discrete circuit components on the substrate (e.g., using a SMT process). For a differential EMG sensor that includes a ground electrode (e.g., as in sensor 200 from FIG. 2), method 500 may be extended to include: depositing a fourth capacitor (222b) on the second surface of the substrate; forming a sixth electrically conductive pathway (213b) that communicatively couples the fifth electrically conductive pathway (211b) and the second electrically conductive pathway (212) through the fourth capacitor (222b); depositing a fourth resistor (232b) on the second surface of the substrate; and forming a seventh electrically conductive pathway (214b) that communicatively couples the fifth electrically conductive pathway (211b) and the second electrically conductive pathway (212) through the fourth resistor (232b). Forming the sixth and seventh electrically conductive pathways may employ established lithography processes. Depositing the fourth capacitor and the fourth resistor may involve soldering discrete circuit components on the substrate (e.g., using a SMT process).

Capacitive EMG sensors having sensor electrodes that resistively couple to the user's skin as described herein may be implemented in virtually any system, device, or process that makes use of capacitive EMG sensors; however, the capacitive EMG sensors described herein are particularly well-suited for use in EMG devices that are intended to be worn by (or otherwise coupled to) a user for an extended period of time and/or for a range of different skin and/or environmental conditions. As an example, the capacitive EMG sensors described herein may be implemented in a wearable EMG device that provides gesture-based control in a human-electronics interface. Some details of exemplary wearable EMG devices that may be adapted to include at least one capacitive EMG sensor from the present systems, articles, and methods are described in, for example, U.S. Provisional Patent Application Ser. No. 61/768,322 (now U.S. Non-Provisional patent application Ser. No. 14/186,889); U.S. Provisional Patent Application Ser. No. 61/857,105 (now U.S. Non-Provisional patent application Ser. No. 14/335,668); U.S. Provisional Patent Application Ser. No. 61/860,063 (now U.S. Non-Provisional patent application Ser. No. 14/276,575); U.S. Provisional Patent Application Ser. No. 61/866,960 (now U.S. Non-Provisional patent application Ser. No. 14/461,044); U.S. Provisional Patent Application Ser. No. 61/869,526 (now U.S. Non-Provisional patent application Ser. No. 14/465,194); U.S. Provisional Patent Application Ser. No. 61/881,064 (now U.S. Non-Provisional patent application Ser. No. 14/494,274); and U.S. Provisional Patent Application Ser. No. 61/894,263 (now U.S. Non-Provisional patent application Ser. No. 14/520,081), all of which are incorporated herein by reference in their entirety.

Throughout this specification and the appended claims, the term "gesture" is used to generally refer to a physical action (e.g., a movement, a stretch, a flex, a pose, etc.) performed or otherwise effected by a user. Any physical action performed or otherwise effected by a user that involves detectable muscle activity (detectable, e.g., by at least one appropriately positioned EMG sensor) may constitute a gesture in the present systems, articles, and methods.

Figure 6:
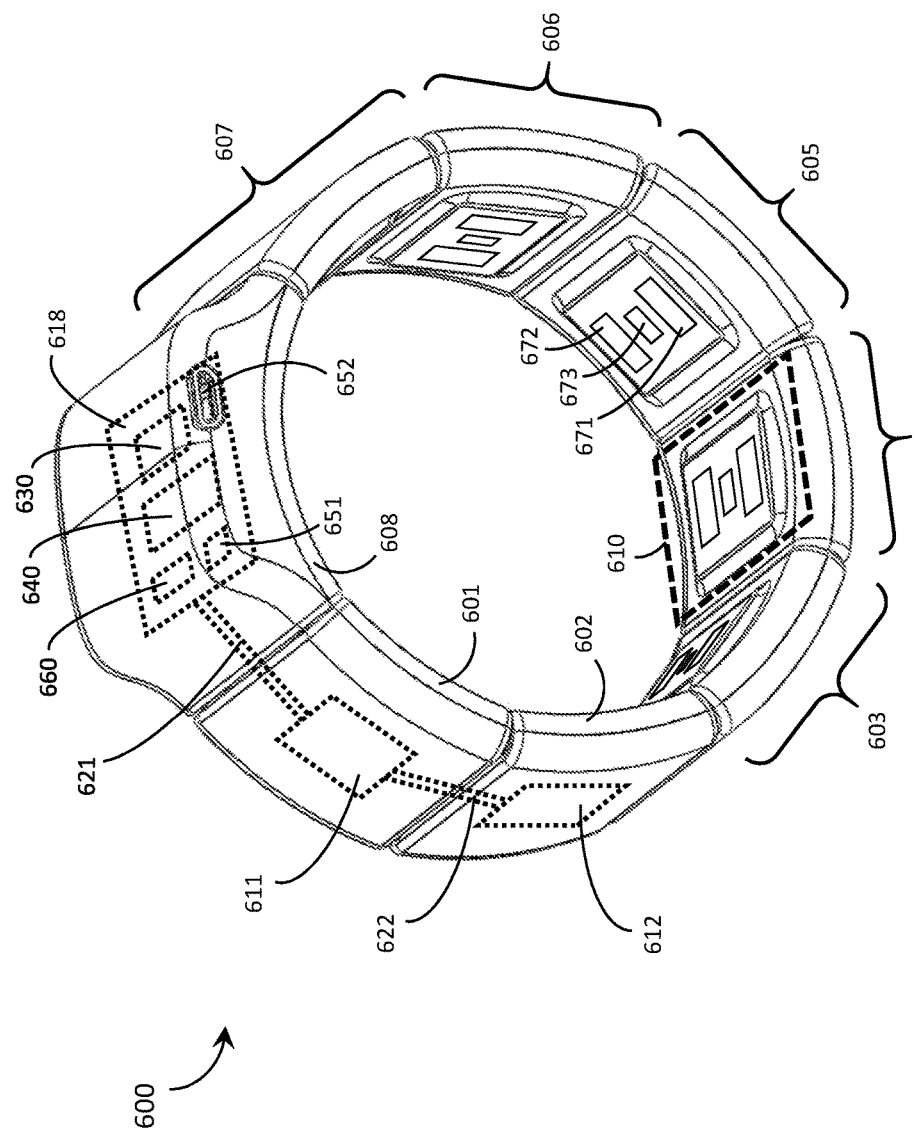
FIG. 6 is a perspective view of an exemplary wearable EMG device that includes capacitive EMG sensors adapted to, in use, resistively couple to the user's skin in accordance with the present systems, articles, and methods.

FIG. 6 is a perspective view of an exemplary wearable EMG device 600 that includes capacitive EMG sensors adapted to, in use, resistively couple to the user's skin in accordance with the present systems, articles, and methods. Exemplary wearable EMG device 600 may, for example, form part of a human-electronics interface. Exemplary wearable EMG device 600 is an armband designed to be worn on the forearm of a user, though a person of skill in the art will appreciate that the teachings described herein may readily be applied in wearable EMG devices designed to be worn elsewhere on the body of the user, including without limitation: on the upper arm, wrist, hand, finger, leg, foot, torso, or neck of the user.

Device 600 includes a set of eight pod structures 601, 602, 603, 604, 605, 606, 607, and 608 that form physically coupled links of the wearable EMG device 600. Each pod structure in the set of eight pod structures 601, 602, 603, 604, 605, 606, 607, and 608 is positioned adjacent and in between two other pod structures in the set of eight pod structures such that the set of pod structures forms a perimeter of an annular or closed loop configuration. For example, pod structure 601 is positioned adjacent and in between pod structures 602 and 608 at least approximately on a perimeter of the annular or closed loop configuration of pod structures, pod structure 602 is positioned adjacent and in between pod structures 601 and 603 at least approximately on the perimeter of the annular or closed loop configuration, pod structure 603 is positioned adjacent and in between pod structures 602 and 604 at least approximately on the perimeter of the annular or closed loop configuration, and so on. Each of pod structures 601, 602, 603, 604, 605, 606, 607, and 608 is physically coupled to the two adjacent pod structures by at least one adaptive coupler (not visible in FIG. 6). For example, pod structure 601 is physically coupled to pod structure 608 by an adaptive coupler and to pod structure 602 by an adaptive coupler. The term "adaptive coupler" is used throughout this specification and the appended claims to denote a system, article or device that provides flexible, adjustable, modifiable, extendable, extensible, or otherwise "adaptive" physical coupling. Adaptive coupling is physical coupling between two objects that permits limited motion of the two objects relative to one another. An example of an adaptive coupler is an elastic material such as an elastic band. Thus, each of pod structures 601, 602, 603, 604, 605, 606, 607, and 608 in the set of eight pod structures may be adaptively physically coupled to the two adjacent pod structures by at least one elastic band. The set of eight pod structures may be physically bound in the annular or closed loop configuration by a single elastic band that couples over or through all pod structures or by multiple separate elastic bands that couple between adjacent pairs of pod structures or between groups of adjacent pairs of pod structures. Device 600 is depicted in FIG. 6 with the at least one adaptive coupler completely retracted and contained within the eight pod structures 601, 602, 603, 604, 605, 606, 607, and 608 (and therefore the at least one adaptive coupler is not visible in FIG. 6).

Throughout this specification and the appended claims, the term "pod structure" is used to refer to an individual link, segment, pod, section, structure, component, etc. of a wearable EMG device. For the purposes of the present systems, articles, and methods, an "individual link, segment, pod, section, structure, component, etc." (i.e., a "pod structure") of a wearable EMG device is characterized by its ability to be moved or displaced relative to another link, segment, pod, section, structure component, etc. of the wearable EMG device. For example, pod structures 601 and 602 of device 600 can each be moved or displaced relative to one another within the constraints imposed by the adaptive coupler providing adaptive physical coupling therebetween. The desire for pod structures 601 and 602 to be movable/displaceable relative to one another specifically arises because device 600 is a wearable EMG device that advantageously accommodates the movements of a user and/or different user forms. As described in more detail later on, each of pod structures 601, 602, 603, 604, 605, 606, 607, and 608 may correspond to a respective housing (e.g., housing 490 of sensor 400) of a respective capacitive EMG sensor adapted to, in use, resistively couple to the user's skin in accordance with the present systems, articles, and methods.

Device 600 includes eight pod structures 601, 602, 603, 604, 605, 606, 607, and 608 that form physically coupled links thereof. Wearable EMG devices employing pod structures (e.g., device 600) are used herein as exemplary wearable EMG device designs, while the present systems, articles, and methods may be applied to wearable EMG devices that do not employ pod structures (or that employ any number of pod structures). Thus, throughout this specification, descriptions relating to pod structures (e.g., functions and/or components of pod structures) should be interpreted as being applicable to any wearable EMG device design, even wearable EMG device designs that do not employ pod structures (except in cases where a pod structure is specifically recited in a claim).

In exemplary device 600 of FIG. 6, each of pod structures 601, 602, 603, 604, 605, 606, 607, and 608 comprises a respective housing, with each housing being akin to a respective one of housing 490 from sensor 400. Each housing may comprise substantially rigid material that encloses a respective inner volume. Details of the components contained within the housings (i.e., within the inner volumes of the housings) of pod structures 601, 602, 603, 604, 605, 606, 607, and 608 are not necessarily visible in FIG. 6 (e.g., the housings may be formed of material that is optically opaque). To facilitate descriptions of exemplary device 600, some internal components are depicted by dashed lines in FIG. 6 to indicate that these components are contained in the inner volume(s) of housings and may not normally be actually visible in the view depicted in FIG. 6, unless a transparent or translucent material is employed to form the housings. For example, any or all of pod structures 601, 602, 603, 604, 605, 606, 607, and/or 608 may include circuitry (i.e., electrical and/or electronic circuitry). In FIG. 6, a first pod structure 601 is shown containing circuitry 611 (i.e., circuitry 611 is contained in the inner volume of the housing of pod structure 601), a second pod structure 602 is shown containing circuitry 612, and a third pod structure 608 is shown containing circuitry 618. The circuitry in any or all pod structures may be communicatively coupled to the circuitry in at least one other pod structure by at least one communicative pathway (e.g., by at least one electrically conductive pathway and/or by at least one optical pathway). For example, FIG. 6 shows a first set of communicative pathways 621 providing communicative coupling between circuitry 618 of pod structure 608 and circuitry 611 of pod structure 601, and a second set of communicative pathways 622 providing communicative coupling between circuitry 611 of pod structure 601 and circuitry 612 of pod structure 602.

Throughout this specification and the appended claims the term "communicative" as in "communicative pathway," "communicative coupling," and in variants such as "communicatively coupled," is generally used to refer to any engineered arrangement for transferring and/or exchanging information. Exemplary communicative pathways include, but are not limited to, electrically conductive pathways (e.g., electrically conductive wires, electrically conductive traces), magnetic pathways (e.g., magnetic media), and/or optical pathways (e.g., optical fiber), and exemplary communicative couplings include, but are not limited to, electrical couplings, magnetic couplings, and/or optical couplings.

Each individual pod structure within a wearable EMG device may perform a particular function, or particular functions. For example, in device 600, each of pod structures 601, 602, 603, 604, 605, 606, and 607 includes a respective capacitive EMG sensor 610 (akin to sensor 200 from FIG. 2, sensor 300 from FIG. 3, and/or sensor 400 from FIG. 4; only one called out in FIG. 6 to reduce clutter) adapted to, in use, resistively couple to the user's skin in accordance with the present systems, articles, and methods. Each capacitive EMG sensor 610 is responsive to muscle activity of the user, meaning that each capacitive EMG sensor 610 included in device 600 to detect muscle activity of a user and to provide electrical signals in response to the detected muscle activity. Thus, each of pod structures 601, 602, 603, 604, 605, 606, and 607 may be referred to as a respective "sensor pod." Throughout this specification and the appended claims, the term "sensor pod" is used to denote an individual pod structure that includes at least one sensor responsive to (i.e., to detect and provide at least one signal in response to) muscle activity of a user.

Pod structure 608 of device 600 includes a processor 630 that processes the signals provided by the capacitive EMG sensors 610 of sensor pods 601, 602, 603, 604, 605, 606, and 607 in response to detected muscle activity. Pod structure 608 may therefore be referred to as a "processor pod." Throughout this specification and the appended claims, the term "processor pod" is used to denote an individual pod structure that includes at least one processor to process signals. The processor may be any type of processor, including but not limited to: a digital microprocessor or microcontroller, an application-specific integrated circuit (ASIC), a field-programmable gate array (FPGA), a digital signal processor (DSP), a graphics processing unit (GPU), a programmable gate array (PGA), a programmable logic unit (PLU), or the like, that analyzes or otherwise processes the signals to determine at least one output, action, or function based on the signals. A person of skill in the art will appreciate that implementations that employ a digital processor (e.g., a digital microprocessor or microcontroller, a DSP, etc.) may advantageously include a non-transitory processor-readable storage medium or memory communicatively coupled thereto and storing data and/or processor-executable instructions that control the operations thereof, whereas implementations that employ an ASIC, FPGA, or analog processor may or may optionally not include a non-transitory processor-readable storage medium, or may include on-board registers or other non-transitory storage structures.

As used throughout this specification and the appended claims, the terms "sensor pod" and "processor pod" are not necessarily exclusive. A single pod structure may satisfy the definitions of both a "sensor pod" and a "processor pod" and may be referred to as either type of pod structure. For greater clarity, the term "sensor pod" is used to refer to any pod structure that includes a sensor and performs at least the function(s) of a sensor pod, and the term processor pod is used to refer to any pod structure that includes a processor and performs at least the function(s) of a processor pod. In device 600, processor pod 608 includes a capacitive EMG sensor 610 (not visible in FIG. 6) adapted to, in use, resistively couple to the user's skin in order to sense, measure, transduce or otherwise detect muscle activity of the user, so processor pod 608 could be referred to as a sensor pod. However, in exemplary device 600, processor pod 608 is the only pod structure that includes a processor 630, thus processor pod 608 is the only pod structure in exemplary device 600 that can be referred to as a processor pod. The processor 630 in processor pod 608 also processes the EMG signals provided by the capacitive EMG sensor 610 of processor pod 608. In alternative embodiments of device 600, multiple pod structures may include processors, and thus multiple pod structures may serve as processor pods. Similarly, some pod structures may not include sensors, and/or some sensors and/or processors may be laid out in other configurations that do not involve pod structures.

In device 600, processor 630 includes and/or is communicatively coupled to a non-transitory processor-readable storage medium or memory 640. Memory 640 may store processor-executable gesture identification instructions that, when executed by processor 630, cause processor 630 to process the EMG signals from capacitive EMG sensors 610 and identify a gesture to which the EMG signals correspond. For communicating with a separate electronic device (not shown), wearable EMG device 600 includes at least one communication terminal. Throughout this specification and the appended claims, the term "communication terminal" is generally used to refer to any physical structure that provides a telecommunications link through which a data signal may enter and/or leave a device. A communication terminal represents the end (or "terminus") of communicative signal transfer within a device and the beginning of communicative signal transfer to/from an external device (or external devices). As examples, device 600 includes a first communication terminal 651 and a second communication terminal 652. First communication terminal 651 includes a wireless transmitter (i.e., a wireless communication terminal) and second communication terminal 652 includes a tethered connector port 652. Wireless transmitter 651 may include, for example, a Bluetooth® transmitter (or similar) and connector port 652 may include a Universal Serial Bus port, a mini-Universal Serial Bus port, a micro-Universal Serial Bus port, a SMA port, a THUNDERBOLT® port, or the like.

For some applications, device 600 may also include at least one inertial sensor 660 (e.g., an inertial measurement unit, or "IMU," that includes at least one accelerometer and/or at least one gyroscope) responsive to (i.e., to detect, sense, or measure and provide at least one signal in response to detecting, sensing, or measuring) motion effected by a user. Signals provided by inertial sensor 660 may be combined or otherwise processed in conjunction with signals provided by capacitive EMG sensors 610.

As previously described, each of pod structures 601, 602, 603, 604, 605, 606, 607, and 608 may include circuitry (i.e., electrical and/or electronic circuitry). FIG. 6 depicts circuitry 611 inside the inner volume of sensor pod 601, circuitry 612 inside the inner volume of sensor pod 602, and circuitry 618 inside the inner volume of processor pod 618. The circuitry in any or all of pod structures 601, 602, 603, 604, 605, 606, 607 and 608 (including circuitries 611, 612, and 618) may include any or all of: an amplification circuit to amplify electrical signals provided by at least one EMG sensor 610, a filtering circuit to remove unwanted signal frequencies from the signals provided by at least one EMG sensor 610, and/or an analog-to-digital conversion circuit to convert analog signals into digital signals. The circuitry in any or all of pod structures 601, 602, 603, 604, 605, 606, 607, and 608 may include one or more discrete component capacitor(s), resistor(s), and/or amplifier(s) in the configuration(s) previously described for sensors 200, 300, and/or 400. Device 600 may also include at least one battery (not shown in FIG. 6) to provide a portable power source for device 600.

Each of EMG sensors 610 includes a respective capacitive EMG sensor responsive to muscle activity corresponding to a gesture performed by the user, wherein in response to muscle activity corresponding to a gesture performed by the user each of EMG sensors 610 provides signals. EMG sensors 610 are capacitive EMG sensors that are adapted to, in use, resistively couple to the user's skin per the present systems, articles, and methods, as described for sensor 200 from FIG. 2, sensor 300 from FIG. 3, or sensor 400 from FIG. 4. In particular, each EMG sensor 610 includes a respective first resistive sensor electrode 671 (only one called out to reduce clutter) that is communicatively coupled to an amplifier (not visible in FIG. 6, but similar to amplifier 250 of sensor 200) through a discrete component capacitor (not visible in FIG. 6, but akin to first capacitor 221a of sensor 200) and a discrete component resistor (also not visible in FIG. 6, but akin to first resistor 231a of sensor 200), a second resistive sensor electrode 672 (only one called out to reduce clutter) that is also communicatively coupled to the amplifier through a discrete component capacitor (not visible in FIG. 6, but akin to third capacitor 221b of sensor 200) and a discrete component resistor (also not visible in FIG. 6, but akin to third resistor 231b of sensor 200), and a ground electrode 673 (only one called out to reduce clutter). Each of the electrodes 671, 672, and 673 of each EMG sensor 610 may be carried by a respective substrate, and the respective circuitry (e.g., 611, 612, and 618) of each pod structure 601, 602, 603, 604, 605, 606, 607, and 608 may be carried by the same substrate and include the communicative pathway, amplifier, capacitor, and resistor elements previously described for sensors 200, 300, and 400. For example, each respective EMG sensor 610 of each pod structure 601, 602, 603, 604, 605, 606, 607, and 608 may include a respective substrate, with the first and second sensor electrodes 671, 672 and the ground electrode 673 of each pod structure 601, 602, 603, 604, 605, 606, 607, and 608 carried by a first surface of the substrate and circuitry 611, 612, 618 carried by a second surface of the substrate, the second surface being opposite the first surface across a thickness of the substrate. For each sensor 610, the circuitry respectively includes at least an amplifier (e.g., 250, 350, 450), a first electrically conductive pathway (e.g., 211a, 311a, 411a) that communicatively couples the first sensor electrode 671 and the amplifier, a first capacitor (e.g., 221a, 321a, 421a) electrically coupled in series between the first sensor electrode 671 and the amplifier in the first electrically conductive pathway, and a first resistor (e.g., 231a, 331a, 431a) electrically coupled in series between the first sensor electrode and the amplifier in the first electrically conductive pathway.

The capacitive EMG sensors 610 of wearable EMG device 600 are differential sensors that each implement two respective sensor electrodes 671, 672 and a respective ground electrode 673, though the teachings herein may similarly be applied to wearable EMG devices that employ single-ended capacitive EMG sensors that each implement a respective single sensor electrode and/or capacitive EMG sensors that share a common ground electrode.

Signals that are provided by capacitive EMG sensors 610 in device 600 are routed to processor pod 608 for processing by processor 630. To this end, device 600 employs a set of communicative pathways (e.g., 621 and 622) to route the signals that are output by sensor pods 601, 602, 603, 604, 605, 606, and 607 to processor pod 608. Each respective pod structure 601, 602, 603, 604, 605, 606, 607, and 608 in device 600 is communicatively coupled to, over, or through at least one of the two other pod structures between which the respective pod structure is positioned by at least one respective communicative pathway from the set of communicative pathways. Each communicative pathway (e.g., 621 and 622) may be realized in any communicative form, including but not limited to: electrically conductive wires or cables, ribbon cables, fiber-optic cables, optical/photonic waveguides, electrically conductive traces carried by a rigid printed circuit board, electrically conductive traces carried by a flexible printed circuit board, and/or electrically conductive traces carried by a stretchable printed circuit board.

Device 600 from FIG. 6 represents an example of a wearable EMG device that incorporates the teachings of the present systems, articles, and methods, though the teachings of the present systems, articles, and methods may be applicable to any wearable EMG device that includes at least one EMG sensor.

Throughout this specification and the appended claims, infinitive verb forms are often used. Examples include, without limitation: "to detect," "to provide," "to transmit," "to communicate," "to process," "to route," and the like.

Unless the specific context requires otherwise, such infinitive verb forms are used in an open, inclusive sense, that is as "to, at least, detect," to, at least, provide," "to, at least, transmit," and so on.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other portable and/or wearable electronic devices, not necessarily the exemplary wearable electronic devices generally described above.

In the context of this disclosure, a memory is a processor-readable medium that is an electronic, magnetic, optical, or other physical device or means that contains or stores a computer and/or processor program. Logic and/or the information can be embodied in any processor-readable medium for use by or in connection with an instruction execution system, apparatus, or device, such as a computer-based system, processor-containing system, or other system that can fetch the instructions from the instruction execution system, apparatus, or device and execute the instructions associated with logic and/or information.

In the context of this specification, a "non-transitory processor-readable medium" can be any element that can store the program associated with logic and/or information for use by or in connection with the instruction execution system, apparatus, and/or device. The processor-readable medium can be, for example, but is not limited to, an electronic, magnetic, optical, electromagnetic, infrared, or semiconductor system, apparatus or device, provided that it is tangible and/or non-transitory. More specific examples (a non-exhaustive list) of the processor-readable medium would include the following: a portable computer diskette (magnetic, compact flash card, secure digital, or the like), a random access memory (RAM), a read-only memory (ROM), an erasable programmable read-only memory (EPROM, EEPROM, or Flash memory), a portable compact disc read-only memory (CDROM), digital tape, and other non-transitory media.

The various embodiments described above can be combined to provide further embodiments. To the extent that they are not inconsistent with the specific teachings and definitions herein, all of the U.S. patents, U.S. patent application publications, U.S. patent applications, foreign patents, foreign patent applications and non-patent publications referred to in this specification and/or listed in the Application Data Sheet, including but not limited to U.S. Non-Provisional Patent Application Ser. No. 14/553,657, U.S. Provisional Patent Application Ser. No. 61/909,786; U.S. Provisional Patent Application Ser. No. 61/768,322 (now U.S. Non-Provisional patent application Ser. No. 14/186,889); U.S. Provisional Patent Application Ser. No. 61/771,500 (now U.S. Non-Provisional patent application Ser. No. 14/194,252); U.S. Provisional Patent Application Ser. No. 61/857,105 (now U.S. Non-Provisional patent application Ser. No. 14/335,668); U.S. Provisional Patent Application Ser. No. 61/860,063 (now U.S. Non-Provisional patent application Ser. No. 14/276,575); U.S. Provisional Patent Application Ser. No. 61/866,960 (now U.S. Non-Provisional patent application Ser. No. 14/461,044); U.S. Provisional Patent Application Ser. No. 61/869,526 (now U.S. Non-Provisional patent application Ser. No. 14/465,194); U.S. Provisional Patent Application Ser. No. 61/881,064 (now U.S. Non-Provisional patent application Ser. No. 14/494,274); U.S. Provisional Patent Application Ser. No. 61/894,263 (now U.S. Non-Provisional patent application Ser. No. 14/520,081), and U.S. Provisional Patent Application Ser. No. 61/903,238 (now U.S. Non-Provisional patent application Ser. No. 14/539,773), are all incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An electromyography ("EMG") sensor comprising:
a first sensor electrode formed of an electrically conductive material, wherein the first sensor electrode comprises a first layer formed of a first electrically conductive material that includes copper and a second layer formed of a second electrically conductive material;
an amplifier; and
a first electrically conductive pathway that communicatively couples the first sensor electrode and the amplifier.

2. The EMG sensor of claim 1 wherein the second electrically conductive material includes a material selected from a group consisting of: gold, steel, stainless steel, silver, titanium, electrically conductive rubber, and electrically conductive silicone.

3. The EMG sensor of claim 1, further comprising:
a ground electrode formed of an electrically conductive material;
a second electrically conductive pathway that communicatively couples to the ground electrode; and
a third electrically conductive pathway that communicatively couples the first electrically conductive pathway and the second electrically conductive pathway.

4. The EMG sensor of claim 1 wherein the EMG sensor is a differential EMG sensor that further comprises:
a second sensor electrode formed of an electrically conductive material, wherein the second sensor electrode comprises a first layer formed of a first electrically conductive material that includes copper and a second layer formed of a second electrically conductive material that includes a material selected from a group consisting of: gold, steel, stainless steel, silver, titanium, electrically conductive rubber, and electrically conductive silicone; and
a second electrically conductive pathway that communicatively couples the second sensor electrode and the amplifier.

5. The EMG sensor of claim 1, further comprising:
a first capacitor electrically coupled in series between the first sensor electrode and the amplifier in the first electrically conductive pathway; and
a first resistor electrically coupled in series between the first sensor electrode and the amplifier in the first electrically conductive pathway.

6. The EMG sensor of claim 1, further comprising:
a housing, wherein the amplifier, the first electrically conductive pathway, and the first layer of the first sensor electrode are all substantially contained within the housing, the housing including a hole, and wherein at least a portion of the second layer of the first sensor electrode extends out of the housing through the hole.

7. The EMG sensor of claim 1, further comprising:
a substrate having a first surface and a second surface, the second surface opposite the first surface across a thickness of the substrate, wherein the first sensor electrode is carried by the first surface of the substrate and the amplifier is carried by the second surface of the substrate.

8. The EMG sensor of claim 7 wherein the first electrically conductive pathway includes at least one electrically conductive trace carried by the second surface of the substrate and at least one via that extends through the substrate.

9. A wearable electromyography ("EMG") device comprising:
at least one EMG sensor responsive to muscle activity corresponding to a gesture performed by a user of the wearable EMG device, wherein in response to muscle activity corresponding to a gesture performed by the user the at least one EMG sensor provides signals, and wherein the at least one EMG sensor includes:
a first sensor electrode formed of an electrically conductive material, wherein the first sensor electrode of the at least one EMG sensor comprises a first layer formed of a first electrically conductive material that includes copper and a second layer formed of a second electrically conductive material;
an amplifier; and
a first electrically conductive pathway that communicatively couples the first sensor electrode and the amplifier;
a processor communicatively coupled to the at least one EMG sensor to process signals provided by the at least one EMG sensor; and
an output terminal communicatively coupled to the processor to transmit signals output by the processor.

10. The wearable EMG device of claim 9 wherein the second electrically conductive material includes a material selected from a group consisting of:
gold, steel, stainless steel, silver, titanium, electrically conductive rubber, and electrically conductive silicone.

11. The wearable EMG device of claim 9 wherein the at least one EMG sensor further includes:
a ground electrode formed of an electrically conductive material;
a second electrically conductive pathway that communicatively couples to the ground electrode; and
a third electrically conductive pathway that communicatively couples the first electrically conductive pathway and the second electrically conductive pathway.

12. The wearable EMG device of claim 9 wherein the at least one EMG sensor includes at least one differential EMG sensor, and wherein the at least one differential EMG sensor further includes:
a second sensor electrode formed of an electrically conductive material, wherein the second sensor electrode of the at least one EMG sensor comprises a first layer formed of a first electrically conductive material that includes copper and a second layer formed of a second electrically conductive material that includes a material selected from a group consisting of: gold, steel, stainless steel, silver, titanium, electrically conductive rubber, and electrically conductive silicone; and
a second electrically conductive pathway that communicatively couples the second sensor electrode and the amplifier.

13. The wearable EMG device of claim 9 wherein the at least one EMG sensor further includes:
a first capacitor electrically coupled in series between the first sensor electrode and the amplifier in the first electrically conductive pathway; and
a first resistor electrically coupled in series between the first sensor electrode and the amplifier in the first electrically conductive pathway.

14. The wearable EMG device of claim 9, further comprising:
at least one housing that at least partially contains the at least one EMG sensor, wherein the amplifier, the first electrically conductive pathway, and the first layer of the first sensor electrode are all substantially contained within the at least one housing, the at least one housing including a hole, and wherein at least a portion of the second layer of the first sensor electrode extends out of the at least one housing through the hole.

15. An electromyography ("EMG") sensor comprising:
a first sensor electrode to couple to a user's skin, wherein the first sensor electrode includes a first layer of a first electrically conductive material that includes copper and a second layer of a second electrically conductive material; and circuitry communicatively coupled to the first sensor electrode.

16. The EMG sensor of claim 15 wherein the second electrically conductive material includes a material selected from a group consisting of: gold, steel, stainless steel, silver, titanium, electrically conductive rubber, and electrically conductive silicone.

17. The EMG sensor of claim 15 wherein the circuitry includes at least a portion of at least one circuit selected from a group consisting of: an amplification circuit, a filtering circuit, and an analog-to-digital conversion circuit.

18. The EMG sensor of claim 17 wherein the circuitry includes:
a high-pass filter that includes a first capacitor and a first resistor; and
a low-pass filter that includes the first resistor and a second capacitor.

19. The EMG sensor of claim 15 wherein a resistive coupling between the first sensor electrode and the user's skin includes an impedance, and wherein the EMG sensor further comprises:
a first resistor to dominate the impedance of the resistive coupling between the first sensor electrode and the user's skin, wherein the first resistor is electrically coupled in series between the first sensor electrode and the circuitry and wherein the first resistor has a magnitude of at least 1 k$\Omega$.

20. The EMG sensor of claim 19 wherein the first resistor has a magnitude of at least 10 k$\Omega$.

21. The EMG sensor of claim 15, further comprising:
a ground electrode to couple to the user's skin, wherein the ground electrode includes a plate of electrically conductive material, and wherein the ground electrode is communicatively coupled to the circuitry.

22. The EMG sensor of claim 15, further comprising:
a first capacitor to galvanically isolate the circuitry from the user's skin, the first capacitor electrically coupled in series between the first sensor electrode and the circuitry.

23. The EMG sensor of claim 15, further comprising:
a housing, wherein the circuitry and the first layer of the first sensor electrode are both substantially contained within the housing, the housing including a hole, and wherein at least a portion of the second layer of the first sensor electrode extends out of the housing through the hole.

24. The EMG sensor of claim 15 wherein the EMG sensor is a differential EMG sensor that further comprises:
a second sensor electrode to couple to the user's skin, wherein the second sensor electrode includes a first layer of the first electrically conductive material that includes copper and a second layer of the second electrically conductive material, wherein the second electrically conductive material includes a material selected from a group consisting of: gold, steel, stainless steel, silver, titanium, electrically conductive rubber, and electrically conductive silicone, and wherein the circuitry is communicatively coupled to the second sensor electrode.

* * * * *

UNITED STATES PATENT AND TRADEMARK OFFICE
CERTIFICATE OF CORRECTION

PATENT NO.         : 10,362,958 B2
APPLICATION NO.    : 16/057573
DATED              : July 30, 2019
INVENTOR(S)        : Cezar Morun et al.

Page 1 of 1

It is certified that error appears in the above-identified patent and that said Letters Patent is hereby corrected as shown below:

In the Specification

At Column 1, Line two, of the Cross-Reference to Related Applications paragraph, please replace "14/533,657" with --14/553,657--.

Signed and Sealed this
Twenty-first Day of January, 2020

Andrei Iancu
*Director of the United States Patent and Trademark Office*